(12) United States Patent
Gupta

(10) Patent No.: US 12,350,450 B2
(45) Date of Patent: *Jul. 8, 2025

(54) SYSTEM AND METHOD FOR CONTROLLED DELIVERY OF MEDICAL DEVICES INTO PATIENT BODIES

(71) Applicant: ANCHOR BALLOON, LLC, Portage, MI (US)

(72) Inventor: Vishal Gupta, Portage, MI (US)

(73) Assignee: Anchor Balloon, LLC, Portage, MI (US)

(*) Notice: Subject to any disclaimer, the term of this patent is extended or adjusted under 35 U.S.C. 154(b) by 975 days.

This patent is subject to a terminal disclaimer.

(21) Appl. No.: 17/301,686

(22) Filed: Apr. 12, 2021

(65) Prior Publication Data

US 2021/0228838 A1     Jul. 29, 2021

Related U.S. Application Data

(63) Continuation-in-part of application No. 16/176,481, filed on Oct. 31, 2018, now Pat. No. 10,980,653.

(51) Int. Cl.
*A61M 25/09* (2006.01)
*A61M 25/00* (2006.01)
*A61M 25/01* (2006.01)

(52) U.S. Cl.
CPC .... *A61M 25/0155* (2013.01); *A61M 25/0053* (2013.01); *A61M 25/09* (2013.01);
(Continued)

(58) Field of Classification Search
CPC .......... A61M 28/0155; A61M 28/0053; A61M 28/09; A61M 28/1006; A61M 28/104;
(Continued)

(56) References Cited

U.S. PATENT DOCUMENTS

| 5,135,536 A | 8/1992 | Hillstead |
| 5,141,494 A | 8/1992 | Danforth et al. |

(Continued)

FOREIGN PATENT DOCUMENTS

| JP | 2015528352 A | 9/2015 |
| JP | WO2016194550 A1 | 6/2017 |

(Continued)

OTHER PUBLICATIONS

Aeby, et al. "A modified technique of balloon anchoring for tricky stent delivery." EuroIntervention, vol. 8, No. 9 (Jan. 2013), pp. 1099-1102. doi: 10.4244/EIJV8I9A168.

(Continued)

*Primary Examiner* — Ryan J. Severson
(74) *Attorney, Agent, or Firm* — Rosenberg, Klein & Lee

(57) ABSTRACT

Intravascular delivery system for deployment of a therapeutic device (such as a stent, and/or other therapeutic devices including balloon catheter(s), laser catheter(s), intravascular ultrasound (IVUS), Optical coherence tomography (OCT), drug delivery catheter(s), coil delivery catheter(s), etc.) as required by a particular surgical procedure, in a controlled and robust manner is supported by a lockable balloon catheter equipped with a locking mechanism configured to lock in vivo to a delivery component, such as a guidewire. The lockable balloon catheter can be controllably transitioned between locked and unlocked modes of operation by inflation/deflation of the balloon of the lockable balloon catheter. The system provides an enhanced interlocking interface between the delivery component and an inner shaft by a unique configuration of the inner shaft. Connection of the inner shaft/guidewire and/or outer shaft/inflation lumen to the balloon is by an extended "neck" at the end(s) of the balloon which snuggly envelopes the portions of the inner and/or outer shaft(s) entering/exiting the balloon, thus avoiding the bonding and simplifying fabrication process.

(Continued)

Being in the locked mode of operation, the lockable balloon catheter facilitates delivery of the therapeutic device along the delivery component to a target site while enhancing the stability of the delivery component, especially near the target site.

20 Claims, 18 Drawing Sheets

(52) U.S. Cl.
CPC ............... *A61M 2025/0059* (2013.01); *A61M 2025/09008* (2013.01); *A61M 2025/09075* (2013.01); *A61M 2025/09166* (2013.01)

(58) Field of Classification Search
CPC ...... A61M 28/0052; A61M 2025/0059; A61M 2025/09008; A61M 2025/09075; A61M 2025/09166; A61M 2025/09125; A61M 2025/0183; A61M 2025/1079
See application file for complete search history.

(56) References Cited

U.S. PATENT DOCUMENTS

| | | |
|---|---|---|
| 5,314,444 A | 5/1994 | Gianturco |
| 6,685,721 B1 | 2/2004 | Kramer |
| 10,314,663 B2 | 6/2019 | Takemoto |
| 10,390,983 B2 | 8/2019 | Nakaya |
| 2003/0028234 A1 | 2/2003 | Miller et al. |
| 2004/0133158 A1 | 7/2004 | Keith et al. |
| 2008/0082050 A1 | 4/2008 | Solar et al. |
| 2010/0125244 A1 | 5/2010 | McAndrew |
| 2018/0036158 A1 | 2/2018 | Nakaya |

FOREIGN PATENT DOCUMENTS

| | | |
|---|---|---|
| JP | 2018019836 A | 2/2018 |
| JP | 2018161415 A | 10/2018 |
| WO | 2014036439 A2 | 3/2014 |

OTHER PUBLICATIONS

Chen, et al. "A simple practical balloon anchoring technique within the guide catheter for chronic total occlusion (CTO) of the coronary artery." J Biomedical Research, vol. 29, No. 5 (Jul. 2015), pp. 423-425. doi: 10.7555/JBR.29.20150068.

Hirokami, et al. "Anchoring technique to improve guiding catheter support in coronary angioplasty of chronic total occlusions." Catheterization and Cardiovascular Interventions, vol. 67, No. 3 (Mar. 2006), pp. 366-371. doi: 10.1002/ccd.20624.

International Search Report and Written Opinion for corresponding PCT Application No. PCT/US2019/052955, mailed Dec. 13, 2019.

International Search Report Issued by Foreign Patent Office in Application No. 2021548507.

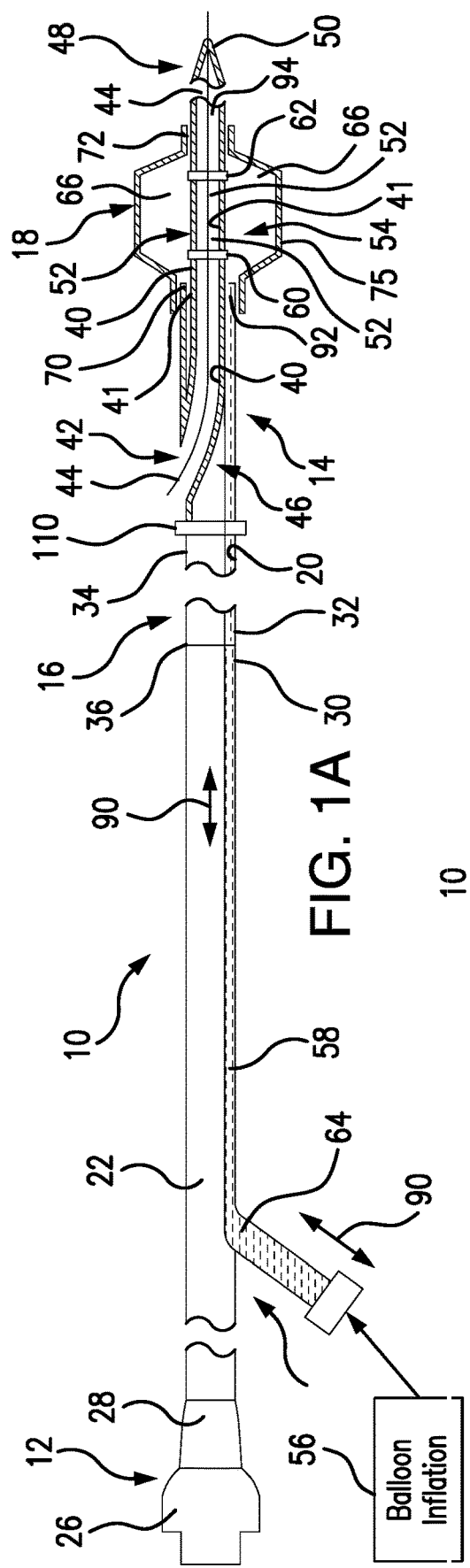

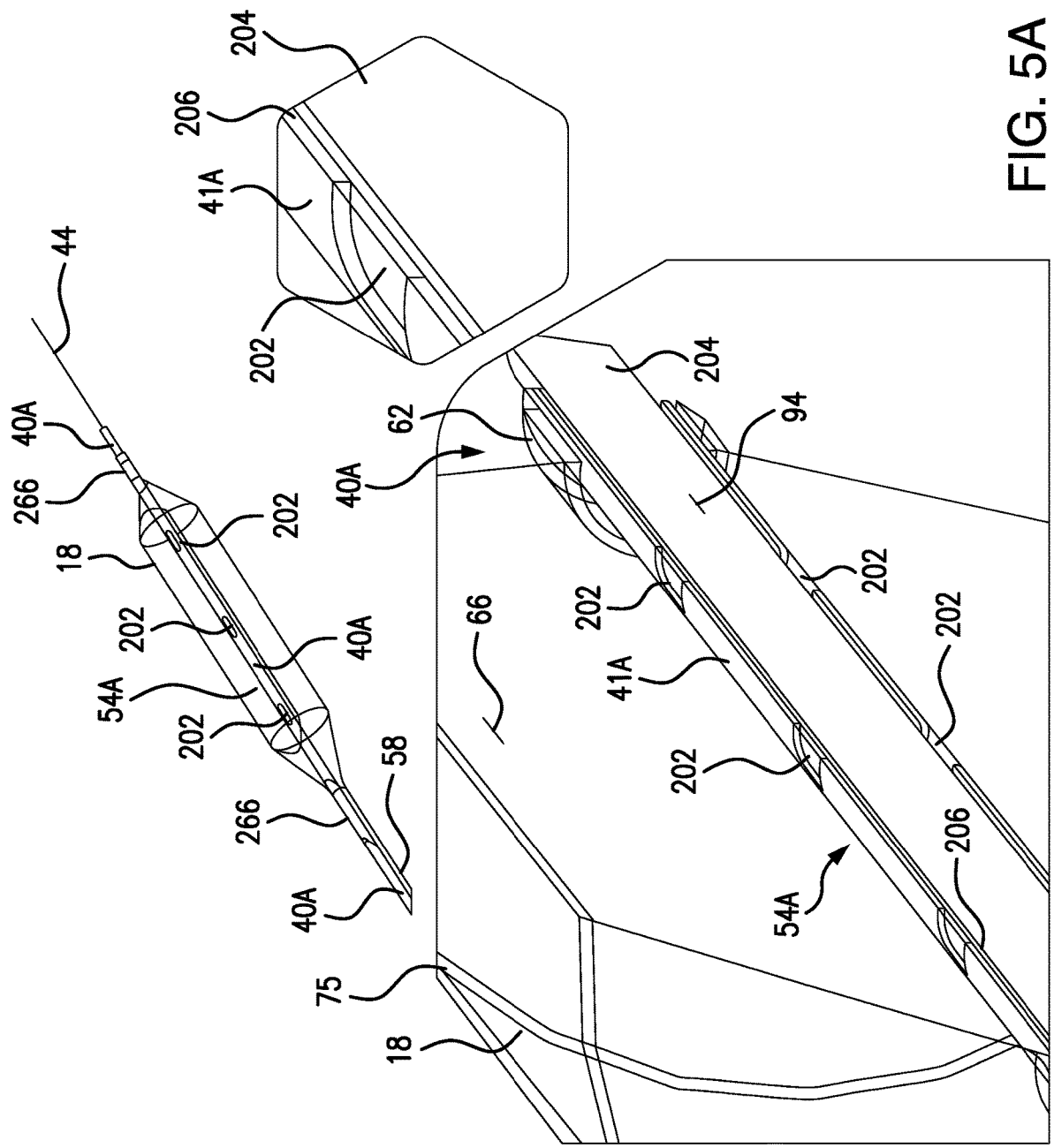

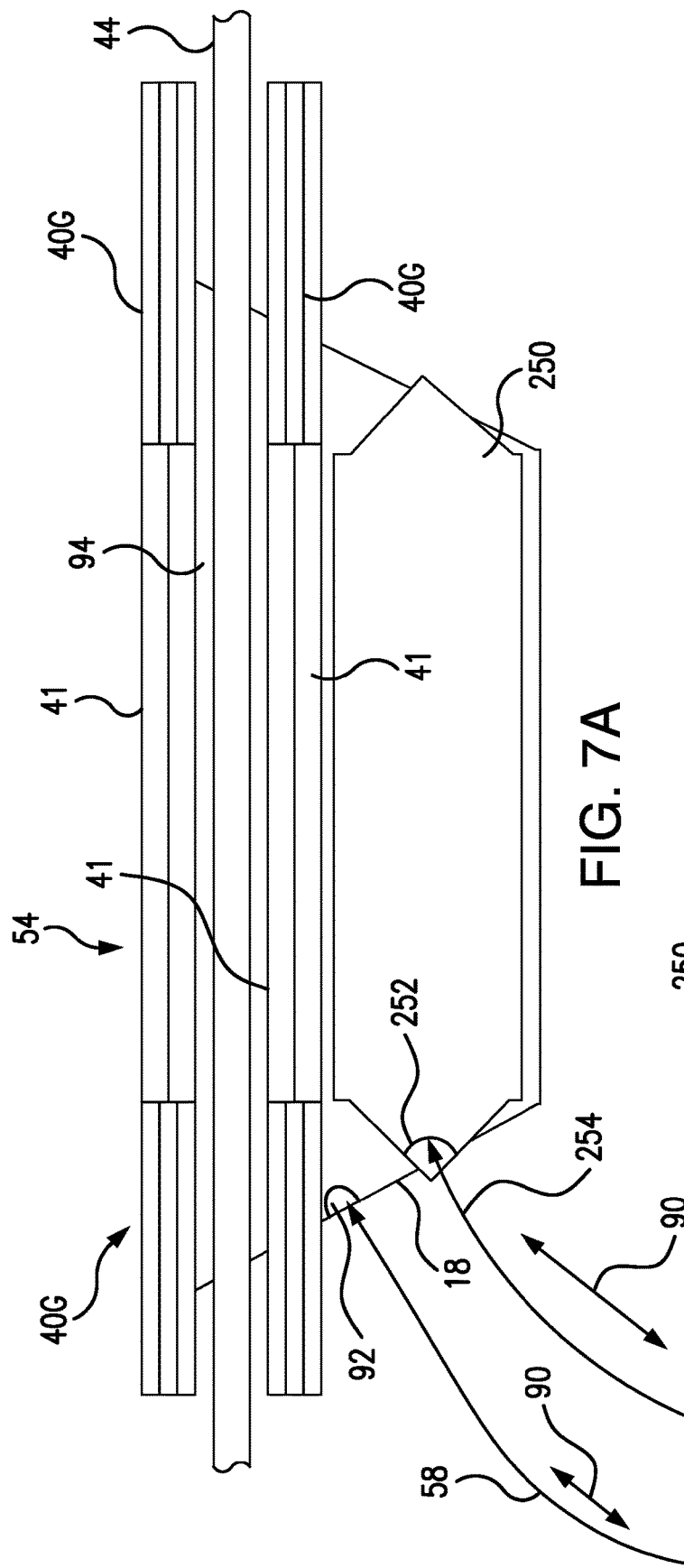
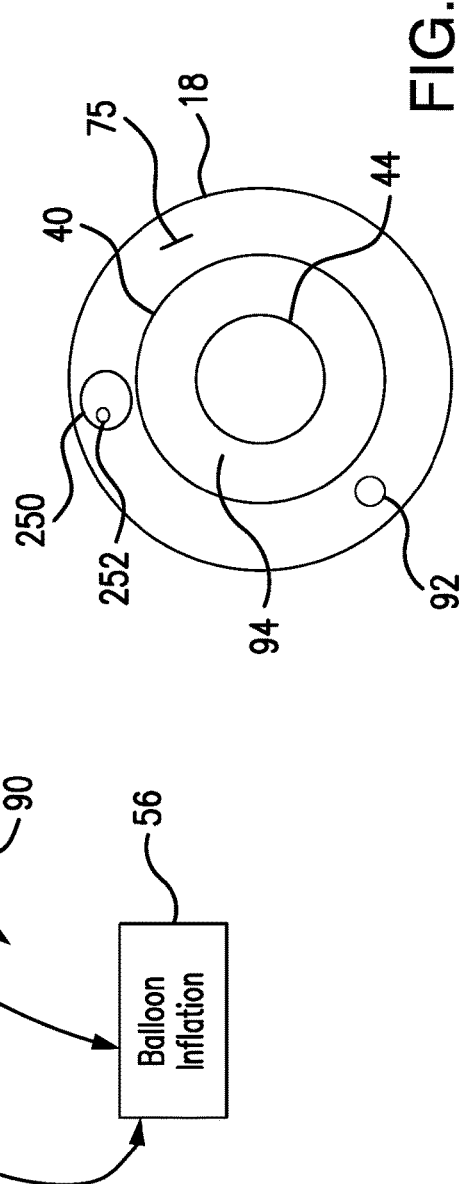
FIG. 7A
FIG. 7B

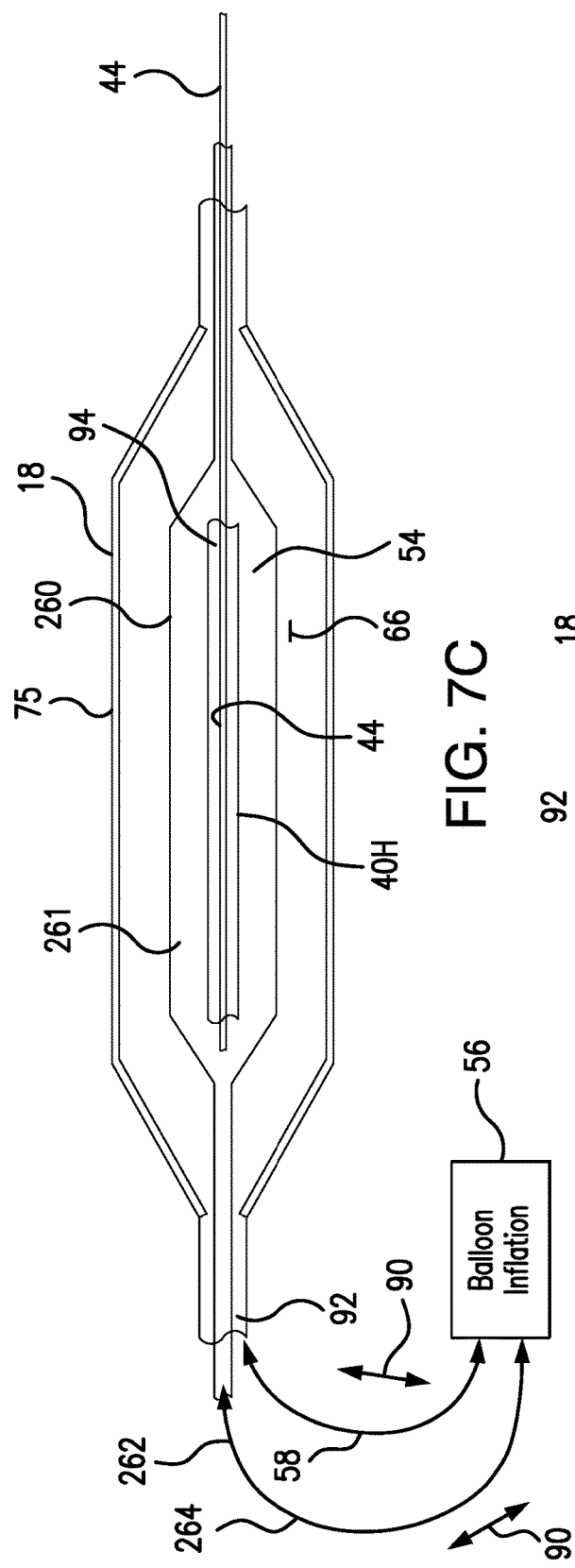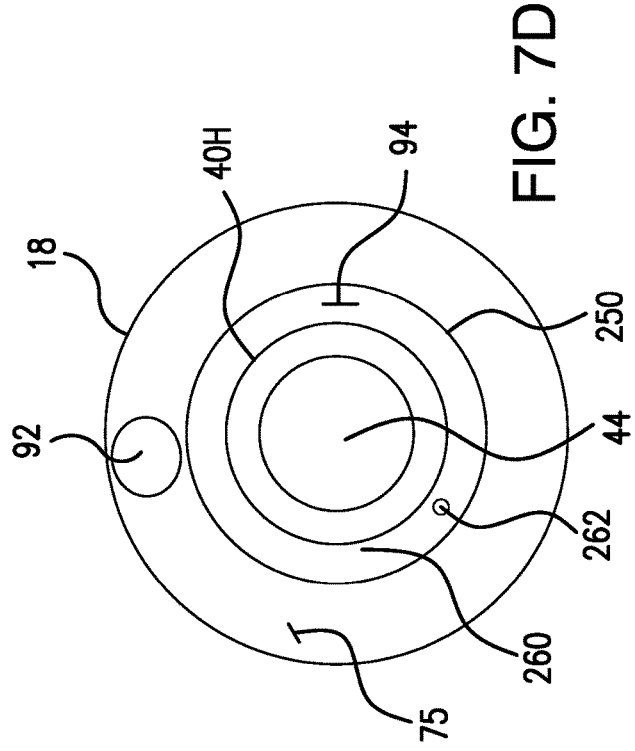

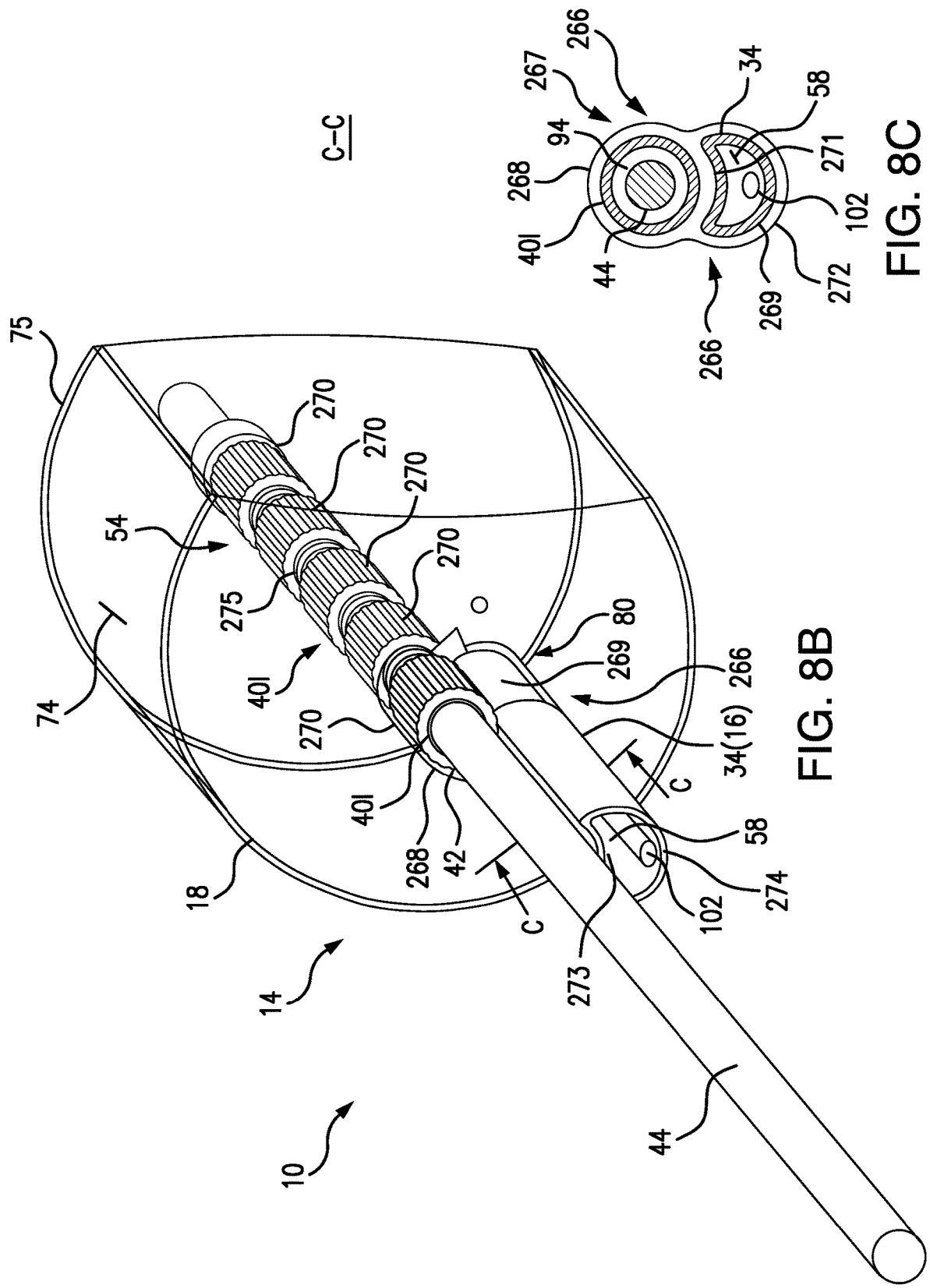

SYSTEM AND METHOD FOR CONTROLLED DELIVERY OF MEDICAL DEVICES INTO PATIENT BODIES

RELATED PATENTS AND APPLICATIONS

This application is a Continuation-in-Part (CIP) of U.S. patent application Ser. No. 16/176,481, filed 31 Oct. 2018.

INCORPORATION BY REFERENCE

The parent patent application Ser. No. 16/176,481 filed 31 Oct. 2018 for "System and Method for Controlled Delivery of Medical Devices into Patient Bodies" is incorporated herein by reference.

FIELD OF THE INVENTION

The present invention is directed to medical devices, such as, for example, minimally invasive devices applicable for treatment within the human (or animal) body internal passages, such as, for example, vasculature (such as blood vessels), or bile duct, as well as renal ureteric duct, etc., and in particular, to a delivery system for percutaneous coronary intervention adapted, for example, for intravascular balloon angioplasty.

More in particular, the present invention addresses medical devices designed for intravascular deployment of therapeutic elements, using a balloon catheter, that is in vivo securely lockable in a controlled manner to a delivery component, such as a guidewire.

In overall concept, the present invention is directed to a system and method for deployment of a therapeutic element, such as, for example, a stent (as well as other therapeutic elements including balloon catheter(s), laser catheter(s), intravascular ultrasound (IVUS), Optical coherence tomography (OCT), drug delivery catheter(s), coil delivery catheter(s), etc.), using a balloon catheter in a patient's body internal passages (for example, intravascular, or other internal tube-like structures) in a controlled robust manner which permits a reduction of a number of equipment exchanges needed to deploy the therapeutic element at a lesion site within an internal tube-like structure (for example, a blood vessel) in a patient's body while locking the balloon catheter to a delivery component (such as, for example, a guidewire), as well as securing the guidewire within the blood vessel during advancement of the therapeutic element to and beyond the lesion site.

In addition, the present system is directed to a balloon catheter which is provided with a locking mechanism for controllable locking in vivo to a delivery component, e.g., a guidewire, inserted into the blood vessel under treatment, where the locked balloon catheter facilitates delivery of additional components (such as a therapeutic delivery catheter) along the guidewire to a target site for treatment while enhancing the stability of the guidewire within the blood vessel as required by a defined procedure.

The present invention is also directed to an intravascular delivery system supported by a balloon catheter equipped with a mechanism to anchor and stabilize a guidewire near the target site for superior delivery of additional intravascular components along the guidewire by minimizing movement of the distal end of the guidewire within the blood vessel, thereby enhancing guidewire stability in vivo.

Furthermore, the present invention is directed to an intravascular kink resistant delivery system which is reinforced by an internal enforcement mechanism, such as, for example, a core wire to facilitate the advancement of the intravascular delivery system, as well as the additional intravascular device (such as a stent) to the target site in the blood vessel of interest, with the core wire equipped with at least one marker band for an enhanced visualization of the system position in the blood vessel.

The present system is further directed to a balloon catheter which has a uniquely configured inner shaft cooperating with a balloon and providing enhanced locking cooperation with the guidewire when the balloon is controllably pressurized as required by surgical procedure.

The present invention additionally is directed to a balloon catheter which is configured with seamless transitions between cooperating elements to provide a smooth miniaturized longitudinal profile to ease the advancement of the system inside the blood vessel under treatment in the least traumatic manner.

Additionally, the present system addresses a balloon catheter implemented with a double-balloon sub-system for an improved controllability in stabilizing of the balloon catheter to the guidewire.

The subject system further addresses a balloon catheter equipped with a balloon system which is uniquely designed with an extended "neck" of the balloon integral with the balloon body and fabricated from the balloon material, where the balloon's extended "neck" snuggly envelopes the parallel low profile distal outer shaft (defining an inflation channel) and the inner shaft (defining the guidewire lumen and carrying the balloon thereon) connected with the balloon and coupled thereto by, for example, heat shrinking of the extended "neck" of the balloon around the distal outer shaft and inner shaft.

Furthermore, the present invention is directed to a method of using the delivery system where a balloon on a balloon catheter is delivered to (or beyond) a target site in a blood vessel over a guidewire, and the balloon is inflated via an inflation mechanism to dilate the blood vessel and disrupt the lesion. The balloon subsequently may be deflated, and displaced adjacent to the lesion at the target site. The balloon catheter is subsequently locked to the guidewire by re-inflating the balloon. One or more additional intravascular components may be delivered to the lesion, while the balloon catheter remains locked to the guidewire which is anchored and stabilized within the blood vessel, as required by a defined procedure.

BACKGROUND OF THE INVENTION

Ischemic cardiovascular syndromes affect blood flow by narrowing, weakening, or blocking a blood vessel, often resulting from the buildup of material (referred to herein as a lesion) within the blood vessel. Ischemic cardiovascular syndromes may include the coronary vascular syndrome, sometimes referred to as coronary artery disease (CAD), generally associated with blood vessels leading to/from the heart, as well as the peripheral vascular syndrome, commonly referred to as the peripheral artery disease (PAD), associated with blood vessels which do not lead to/from the heart or the brain.

Endovascular treatment for ischemic cardiovascular syndromes permits access to vascular lesions through percutaneous introduction of catheters through a blood vessel, such as, for example, the femoral artery, and therefore involves less patient trauma than an open surgical approach.

Percutaneous transluminal angioplasty of coronary and peripheral arteries (PTCA and PTA, respectively) are widely accepted as the revascularization procedures of choice in patients with ischemic cardiovascular syndromes (e.g., chronic and acute coronary ischemic syndromes) and peripheral ischemic syndromes (such as the chronic limb ischemia, including claudication and critical limb ischemia).

However, the use of the conventional percutaneous treatments may be limited due to re-occlusion or restenosis. This may be due to the exuberant proliferation of smooth muscle cells that grow to occlude the treated vessel segment, progression of atherosclerotic plaque or negative remodeling of the treated segment causing reoccurrence of symptoms. Re-occlusion, or restenosis, may necessitate potential re-intervention for additional treatment.

Various adjuncts to angioplasty seek to reduce restenosis through numerous techniques. These techniques may include extractional, rotational, orbital, or laser atherectomy, as well as the use of bare metal and bare nitinol stents. More recently, drug eluting stents (DES) began to be used to treat/prevent restenosis. The latter technology has been demonstrated to significantly reduce coronary artery restenosis when compared to angioplasty or bare metal stents.

In peripheral arteries, the use of bare nitinol stents has been shown to be superior to balloon angioplasty alone and has emerged as the "default" percutaneous strategy for the treatment of chronic limb ischemic syndromes, particularly in complex disease patterns involving the femoropopliteal artery.

Stents have been customarily used for treating occlusive vascular disease. For example, U.S. Pat. No. 5,135,536 to Hillstead and U.S. Pat. No. 5,314,444 to Gianturco describe a stent which comprises an expandable wire tube having a reduced diameter for transluminal placement. Once the stent is positioned within a vessel, a balloon catheter is used to expand the stent to support and reinforce the full circumference of the vessel. Such prior art stents typically have high radial strength to resist collapse due to vessel disease.

In the conventional procedure for a stent delivery following percutaneous transluminal angioplasty, initially a guidewire is percutaneously advanced to the lesion within a blood vessel. Subsequently, an angioplasty balloon catheter is advanced over the guidewire to the lesion. The angioplasty balloon catheter may be advanced in an over-the-wire ("OTW") manner or in a rapid exchange ("RX") operation. When in place, the balloon is inflated to expand the blood flow channel within the blood vessel at the lesion site.

In a subsequent step, the angioplasty balloon catheter is removed from the blood vessel while the guidewire remains in place, and a stent delivery balloon catheter is advanced over the guidewire to the lesion for stent delivery.

A drawback of the conventionally performed procedure is the limited safety and the difficulty of advancing the stent delivery balloon catheter across the lesion, even subsequent to the angioplasty due to the fact that the guidewire does not always constitute a sufficiently stable structure for catheter advancement in the blood vessel. For example, the free distal tip of the guidewire can uncontrollably move around within the blood vessel. The uncontrollable motion of the distal end of the guidewire may cause its retraction into the guidewire lumen in the stent delivery balloon catheter during advancement within the vessel. This may happen when the blood vessel is tortuous, diffusely diseased, severely calcified, or when there is reduced support from the guiding catheter. If a clinician attempts to advance the stent delivery balloon catheter along an unstable distal free tip of the guidewire, there is a risk of vessel damage, including vessel dissection. Accordingly, a clinician often needs to remove the stent delivery balloon catheter and reintroduce an angioplasty balloon catheter over the guidewire to perform additional angioplasty procedures. This exposes an additional risk for the patient health, reduces efficiency of the procedure, abandonment without placement of the therapeutic device and is extremely expensive.

Given a growing patient population with conditions associated with a substantial vessel wall calcification, especially in patients suffering diabetes and/or chronic kidney disease, the need for effective intravascular therapies increases dramatically. There is a patient population in which current therapies may be inefficient and/or ineffective. Thus, there is a need for an improved intravascular technology that permits intravascular deployment of a therapeutic element, such as a stent, in a controlled and robust manner.

One of improved systems for controlled delivery of medical devices into a patient body is presented in a co-pending U.S. patent application Ser. No. 16/176,481 (incorporated herein by reference), filed on 31 Oct. 2018, authored by Dr. Vishal Gupta, which addresses an intravascular delivery system using a lockable balloon catheter equipped with a locking mechanism operated controllably to anchor and stabilize the guidewire in proximity to the target site within a blood vessel under treatment for superior delivery of additional intravascular components along the guidewire, resulting in a reduced displacement of the distal end of the guidewire within the blood vessel, thus attaining an enhanced guidewire stability, in vivo.

The present system constitutes a further development in the field of intravascular delivery systems.

SUMMARY OF THE INVENTION

It is therefore an object of the present invention to provide an intravascular delivery system using a lockable balloon catheter equipped with a controllable locking mechanism operated to anchor/stabilize the guidewire near the target site within the blood vessel for superior delivery of additional intravascular components along the guidewire, resulting in a minimal (if at all) displacement of the distal end of the guidewire within the blood vessel, thus attaining an enhanced guidewire stability in vivo.

It is another object of the present invention to provide a system and a method for deployment of a therapeutic element (such as a stent) in a tube-like internal structure in a patient's body, for example intravascular, or other, passages, such as the bile duct or ureteric duct, in a controlled and robust manner that would support a reduced number of equipment exchanges needed to deploy the therapeutic device in proximity to a lesion site within a blood vessel, while efficiently securing a balloon catheter to a delivery component (such as a guidewire) by a uniquely configured locking mechanism having an increased gripping interface with the guidewire, as well as anchoring the guidewire within the blood vessel during the advancement of the therapeutic element to the lesion site.

It is a further object of the present invention to provide a robust locking mechanism for releasably securing the balloon catheter in vivo to a delivery component, e.g., a guidewire, so that the balloon catheter, being anchored to the guidewire, facilitates delivery of additional components, e.g., a therapeutic delivery catheter, along the guidewire to a target site, enhanced by the stability of the guidewire in the blood vessel, especially near the target site.

It is an additional object of the present invention to provide an intravascular delivery system which prevents the guidewire's distal end from uncontrollable motion throughout the vessel lumen, providing sufficient rigidity and stability of the guidewire in proximity to the target (lesion) site within a blood vessel, which is beneficial for delivery of a therapeutic element, e.g., a stent, to the target site.

It is also an object of the present invention to provide a method of using the subject balloon catheter controllably lockable to a guidewire within the blood vessel of interest for delivering the balloon catheter to a lesion in the blood vessel over a guidewire, inflating the balloon via a balloon inflation system to pre-dilate the vessel and disrupt the lesion (such as, for example, calcified plaque, disposed on the luminal lining), subsequently deflating the balloon for an additional displacement adjacent to the lesion, and locking the balloon to the guidewire by re-inflating the balloon and actuating the uniquely configured inner shaft into engagement with the guidewire with an increased gripping interface therebetween. One or more additional intravascular components may be subsequently delivered to the lesion site while the subject balloon catheter remains locked to the guidewire which, in its turn, is securely anchored and stabilized within the vessel during the procedure.

In addition, it is an object of the present invention to provide a kink resistant intravascular delivery system enhanced with additional support, such as a core wire with a marker band, for a flexible but kink resistant advancement of the balloon catheter along the guidewire and with an enhanced visualization during procedure.

It is a further object of the present invention to provide a balloon catheter equipped with an uniquely shaped balloon member having an extended proximal "neck" (as well as the distal "neck") integral with the balloon body which snuggly envelopes the inner and outer shafts at their connection area to the balloon, where the inner and outer shafts extend in parallel and in a low profile matching interconnecting relationship to one another.

In accordance with one aspect of the subject system, an intravascular system is provided for securely advancing a therapeutic device, such as, for example, a stent (as well as other therapeutic devices including balloon catheter(s), laser catheter(s), intravascular ultrasound (IVUS), Optical coherence tomography (OCT), drug delivery catheter(s), coil delivery catheter(s), etc.), over a guidewire to (or beyond) a lesion within a blood vessel (or the bile duct or the ureteric duct) of a patient. The subject system includes an elongated catheter shaft (outer shaft) having a proximal portion and a distal portion coupled to the balloon system (between the proximal and distal sections thereof). An inflation lumen extends internal the elongated catheter shaft between the proximal and the distal sections. A guidewire lumen (inner shaft) extends between a rapid-exchange (RX) port formed within the elongated catheter shaft and a distal end of the balloon catheter.

The balloon system is affixed to the distal portion of the elongated catheter shaft (outer shaft) and positioned in alignment and cooperation with a predetermined portion (locking portion) of the inner shaft. The balloon system may be operated, in a controlled manner, to assume an inflated (pressurized) or a deflated (de-pressurized) state, respectively. A proximal end of the balloon system may be positioned a short distance of about 5 mm-30 mm apart from the rapid-exchange (RX) port (also be referred to herein as a proximal guidewire port). This arrangement is beneficial for stability in advancement of the therapeutic device (for example, a stent) along the guidewire to (or beyond) the lesion site within the blood vessel proximal to the rapid-exchange port while the balloon remains inflated within the blood vessel.

The locking portion of the inner shaft is disposed inside the balloon system and extends between the proximal and distal ends of the balloon system. The locking portion of the inner shaft may be configured to transition within the balloon system between an unlocked mode of operation, when the inner shaft is not engaged contiguous with the guidewire extending therewithin, and a diameter of the guidewire lumen (inner shaft) is sized to permit its slidable displacement relative to the guidewire disposed within the guidewire lumen, and a locked mode of operation. In the locked mode of operation, the locking portion of the inner shaft is compressed within the balloon system to reduce the diameter of the guidewire lumen (inner shaft), so that the walls of the guidewire lumen are contiguous with the guidewire and become circumferentially coupled to and compress the guidewire to "anchor" the guidewire within the guidewire lumen.

In order to provide an enhanced "guidewire gripping" (anchoring) capability, the inner shaft in the present system is uniquely configured. The subject inner shaft (guidewire lumen) has a configuration which creates an enhanced contiguous engagement with a guidewire extending inside the inner shaft when the balloon system is pressurized. In one of numerous alternative implementations, the inner shaft may be configured with slots spaced apart along the length of the inner shaft with an elastomeric layer overlaying an inner surface of the inner shaft. When the balloon system is inflated for anchoring to the guidewire, the elastomeric material within the slots in the walls of the inner shaft is pressed down towards the guidewire, and elastically locks on the guidewire, thus providing an enhanced anchoring of the guidewire within the guidewire lumen. The slots in the walls of the inner shaft provide for a lower pressurizing level to be sufficient to affect the downward displacements of the elastomeric layer for gripping the guidewire.

In another implementation, the inner shaft is machined to remove segments at predetermined areas of the circumference of its outer surface. This arrangement reduces wall thickness of the inner shaft at intervals about the circumference of the inner shaft. The reduced wall thickness provides for a lower collapse pressure to lock the guidewire in position.

In a further embodiment, the inner shaft is configured with a variable wall thickness along its circumference. This arrangement provides for segments (thinner portions of the walls) more easily collapsible when the balloon system is pressurized. This embodiment is characterized by a single lumen extrusion with a sufficient cross-sectional area to maintain sufficient tensile strength at the interface with the guidewire while the walls of the inner shaft can collapse at a specific pressure.

In still another alternative implementation, the inner shaft may be configured with corrugations both at the inner and the outer surfaces. This configuration provides a controllability with a lower pressurizing pressure, as in the arrangement with the variable walls thickness, enhanced by the inner surface corrugations of the inner shaft which are beneficial for an increased gripping capability when in contact with the guidewire inside the inner shaft. The outer surface corrugations provide an enhanced stabilization when engaged with the inner surface of the distal end of the balloon and when in contact with the outer shaft.

In an additional implementation, the inner walls of the inner shaft may be provided with a braiding (canted spring wall concept) to engage the surface of the guidewire, thus providing an anchoring effect for locking the guidewire within the guidewire lumen.

Still further, to improve controllability for the locking mechanism, the present balloon system may be configured with a double balloon arrangement, where an auxiliary balloon may be installed inside the main balloon. The auxiliary balloon may be disposed either coaxially with the main balloon or displaced from the axis of the main balloon. When the main balloon is inflated, the auxiliary balloon may also be inflated to increase the pressure on the walls of the "inner shaft", causing an increased anchoring force applied to the guidewire. Pressurizing of the main and auxiliary balloons may be performed either simultaneously, or separately, as required by the surgical procedure.

The enhanced locking mechanism also may include a modification of the size of the neck portion of the inner shaft in proximity to the rapid-exchange (RX) port. In operation, the narrow neck portion of the inner shaft adjacent to the rapid exchange port locks the guidewire extending within the guidewire lumen at a lower balloon pressurization.

The subject system further includes a proximal hypotube which is secured to the proximal portion of the outer shaft. A core wire (for example, Nitinol wire) extends within the outer shaft with a proximal end bonded to the stainless steel hypotube and the distal end extending beyond the proximal balloon end. The core wire creates a flexible and kink-resistant balloon catheter, that is beneficial in reducing kinking and improving the pushability of the overall system. Marker band(s) may be positioned on the Nitinol core wire for better visualization during the procedure.

The hypotube may be tapered or non-tapered. Preferably, the proximal portion of the outer shaft is swagged to create a smooth, seamless transition between the proximal portion of the outer shaft and the flexible hypotube for reducing the traumatism associated with the procedure.

Even further to reduce the profile of the subject balloon catheter, the proximal end of the balloon is configured with a somewhat "eight"-shaped "neck" where the inner shaft with the guidewire enters the upper portion of the "eight"-shaped "neck", while the outer shaft with the inflation lumen enters the lower portion of the "eight"-shaped "neck". The inner shaft and the inflation channel may extend parallel each to the other in a matching configuration for producing a reduced profile. The "eight"-shaped "neck" extends over the inner shaft/outer shaft's connection with the balloon. The balloon extended "neck" snuggly embraces (envelopes) the inner/outer shafts entrance into the balloon, and may be heat shrunk to secure the inner/outer shafts to the balloon, thus simplifying the bonding process. The parallel extension of the inner/outer shafts and lower profile of the design is beneficial for pushability of the subject catheter during the surgical procedure and permits a simplified fabrication process.

The balloon may be shaped with a smoothing radius between the balloon body and the balloon necks, both at the distal end proximal ends, to improve the wrapping profile and for an easier removal from the artery and the outer shaft.

The locking portion of the inner shaft may include the afore-presented configurations. In addition, the walls of the inner shaft may be fabricated from a highly flexible material to facilitate the compression of the guidewire. The flexible material may be enhanced by a braided material. The braided material may be a metal composition with the braided material coated with a polymer such that the locking portion of the inner shaft within the balloon is fluid impermeable.

The balloon catheter may have radiopaque markers disposed along the inner shaft, as well as the Nitinol core wire. The radiopaque markers may be also positioned adjacent to the rapid-exchange port.

In accordance with another aspect of the subject system, a method is provided for safe advancement of an intravascular delivery system over a guidewire along the balloon shaft to a lesion within a blood vessel of a patient. The method may include the steps of:

providing a balloon catheter lockable to a guidewire within the blood vessel. The lockable balloon catheter includes a first shaft having a proximal portion and a distal portion, a balloon attached to the first shaft, and an inflation lumen system extending in the first shaft between its proximal portion and the balloon. A second shaft extends distally from a rapid-exchange (RX) port inside the balloon to a distal end of the balloon catheter to form a guidewire lumen.

A balloon system is affixed to the first shaft at the distal portion thereof such that a proximal end of the balloon is displaced from the rapid-exchange port a short distance of about 5 mm-30 mm to attain a stable advancement of the therapeutic element (stent) over the delivery component (such as a guidewire system) to the target site within the body lumen proximal to the rapid-exchange port while the balloon remains inflated within the body lumen.

The second shaft (also referred to herein as a guidewire lumen) is configured to transition within the balloon system from an unlocked mode of operation (when a diameter of the second shaft is sized to permit the slidable movement of the guidewire therein, to a locked state (when a portion of the second shaft aligned with the balloon is compressed to reduce the diameter of the second shaft to circumferentially engage the guidewire to lock the guidewire within the second shaft (guidewire lumen), responsive to pressurization within the balloon system.

The subject method further includes the steps of:

delivering the lockable balloon catheter to the lesion in the blood vessel over the guidewire, inflating the balloon system of the lockable balloon catheter to dilate the blood vessel and disrupt the lesion, deflating the balloon system, displacing the deflated balloon system on the balloon catheter past the lesion within the blood vessel, and locking the balloon catheter to the guidewire by re-inflating the balloon, thus causing the walls of the guidewire lumen to grip the guidewire and thus to anchor the balloon catheter to the guidewire.

Inflating the balloon compresses the walls of the guidewire lumen within the balloon around the guidewire to lock the guidewire in place, and thus locks the balloon catheter to the guidewire.

The subject method further continues by delivering another catheter (for example, a stent catheter, or other therapeutic devices including balloon catheter(s), laser catheter(s), intravascular ultrasound (IVUS), Optical coherence tomography (OCT), drug delivery catheter(s), coil delivery catheter(s), etc.) over the guidewire to the lesion site while the lockable balloon catheter remains locked to the guidewire to anchor and stabilize the guidewire within the blood vessel.

The subject system and method reduces the number of equipment exchanges needed to deploy the therapeutic devices at a lesion site within the blood vessel, while securing the delivery component within the blood vessel during advancement of the therapeutic catheter to the lesion site.

These and other objects and advantages of the subject system and method will become more apparent to a person of ordinary skill in the art upon reading the Detailed Description of the Subject Invention in conjunction with the Patent Drawings.

BRIEF DESCRIPTION OF THE DRAWINGS

FIGS. 1A-1C depict a subject lockable balloon catheter, partially in cross-section with FIG. 1A representative of the subject catheter system in a deflated state, FIG. 1B representative of the subject catheter balloon in the inflated state, and FIG. 1C detailing the subject catheter from the proximal guidance port to the distal balloon neck;

FIGS. 5A-5E show schematically alternative embodiments of the inner shaft, with FIG. 5A showing the slotted inner shaft configuration, FIG. 5B depicting the inner shaft with segments removed, FIG. 5C depicting another embodiment of the inner shaft with variable wall thickness, 5D being representative of an alternative embodiment of the inner shaft with corrugations on the inner and outer surfaces, and FIG. 5E being representative of the concept of the canted spring wall concept for the inner shaft;

FIGS. 7A-7D are representative of the double balloon concept for the present system with FIGS. 7A-7B depicting the off-axis auxiliary balloon, and FIGS. 7C-7D showing a two-balloon system with inner (auxiliary) balloon coaxial) with the main balloon;

FIGS. 8A-8B are representative of two views of the subject balloon system with the balloon "neck" enveloping the inner shaft (with the guidewire extending therewithin) and the inflation channel which cooperate for the low profile;

FIG. 8C shows a cross-section of FIG. 8B taken along lines C-C;

DETAILED DESCRIPTION OF THE PREFERRED EMBODIMENT

Figure 1C:
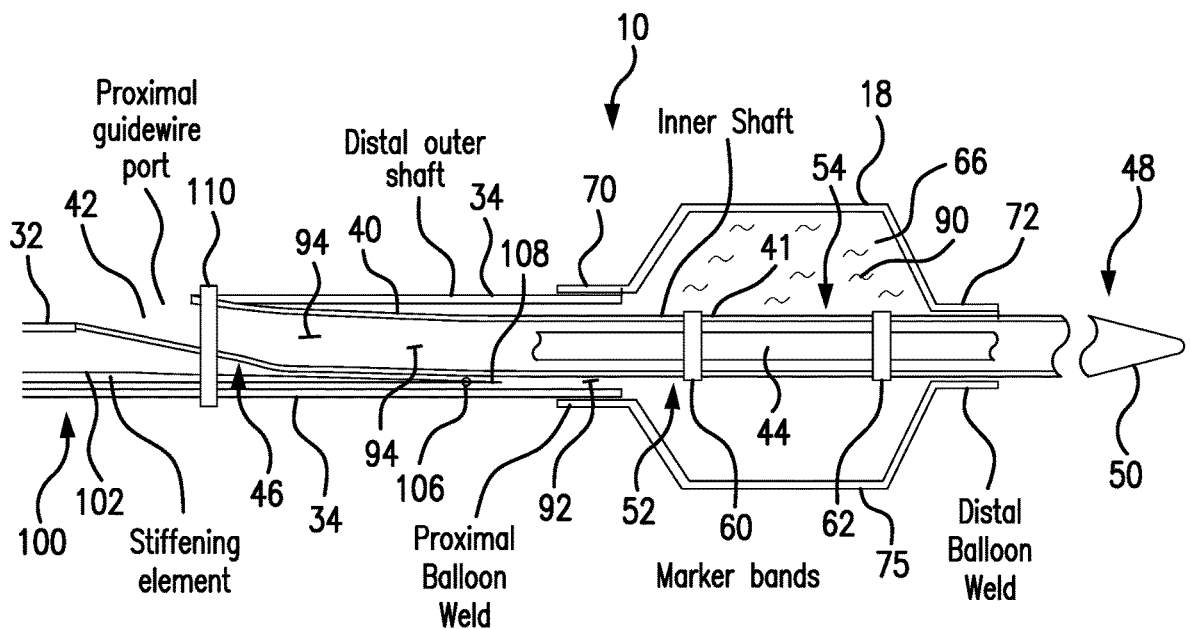

Referring to FIGS. 1A-1C, 3-4 and 11A-11L, a system and method are developed for deployment of a therapeutic device within a tube-like internal structure (body lumen) of a patient's body (such as, for example, a blood vessel, the bile duct, as well as ureteric duct, etc.). The principles and method of the subject system are applicable for treatment procedures associated with different internal passages within a patient's body. As an example of numerous applications of the subject system design and operation, the description herein addresses intravascular applications for clarity.

The subject system includes a balloon catheter which is capable of locking in position in vivo to a delivery component, such as, for example, a guidewire, disposed within a blood vessel. Subsequent to locking of a lockable balloon catheter to the guidewire, another catheter for delivery of a therapeutic device, such as a stent (as well as other therapeutic devices, including but not limited to balloon catheter (s), laser catheter(s), intravascular ultrasound (IVUS), Optical coherence tomography (OCT), drug delivery catheter(s), coil delivery catheter(s), etc.), may be advanced over the guidewire to a target site in the blood vessel while the locking balloon catheter stably anchors the guidewire in place adjacent to the target site in the blood vessel.

The subject system is particularly well-suited for treating conditions associated with vessel wall tortuosity, diffuse disease, calcification or poor guiding catheter support during ischemic cardiovascular syndromes including the coronary vascular syndrome, sometimes referred to as coronary artery disease (CAD), as well as the peripheral vascular syndrome, sometimes referred to as the peripheral artery disease (PAD).

Referring to FIGS. 1A-1C, 3, 4, 10A-10D, and 11A-11L, the subject intravascular delivery system includes a balloon catheter 10 which has a proximal region 12 and distal region 14. An elongated outer shaft 16 extends between the proximal region 12 and the distal region 14 of the balloon catheter 10. A balloon system (which includes at least one balloon 18) is secured to the elongated outer shaft 16 of the balloon catheter 10.

The proximal region 12 of the balloon catheter 10 is represented by a hypotube 22 terminating, at its proximal end 24, to a Luer valve 26 via a strain relief unit 28. A distal end 30 of the hypotube 22 is connected to the outer shaft 16. The Luer 26 may serve as a handle for helping a clinician to manipulate the lockable balloon catheter 10.

The outer shaft 16 has a proximal portion 32 and a distal portion 34. The proximal portion 32 of the outer shaft 16 is connected to the distal end 30 of the hypotube 22. In order to provide a smooth low-profile seamless transition between the outer surface of the proximal end 24 of the hypotube 22 and the proximal portion 32 of the outer shaft 16, the hypotube is machined to form a swagged segment 36, best presented in FIGS. 10A and 10C, as well as 10D, as will be detailed in further paragraphs. The proximal portion 32 of the outer shaft 16 may be attached to the swagged segment 36 of the hypotube 22 by any appropriate technique including, for example, bonding, gluing, etc.

An inner shaft (also referred to herein as a guidewire lumen) 40, as shown in FIGS. 1A-2C, 3, 5A-7A, and 8A-8B, extends between a proximal guidewire port 42 (also referred to herein as rapid exchange (RX) port), along the distal region 14 of the balloon catheter 10, and terminates at a distal tip 50. The inner shaft 40 extends inside the balloon 18 and additionally constitutes the guidewire lumen to provide the sliding advancement of the balloon catheter 10 over a guidewire 44.

Figure 11A:
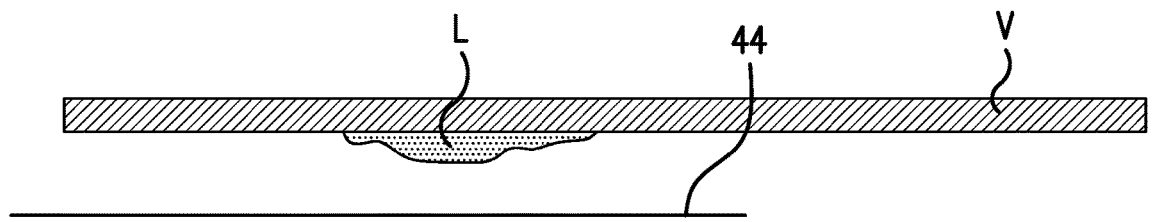
FIGS. 11A-11L illustrate the exemplary steps of the intravascular delivery procedure using the subject lockable balloon catheter to deliver a therapeutic device to a target site within a blood vessel.
Figure 11B:
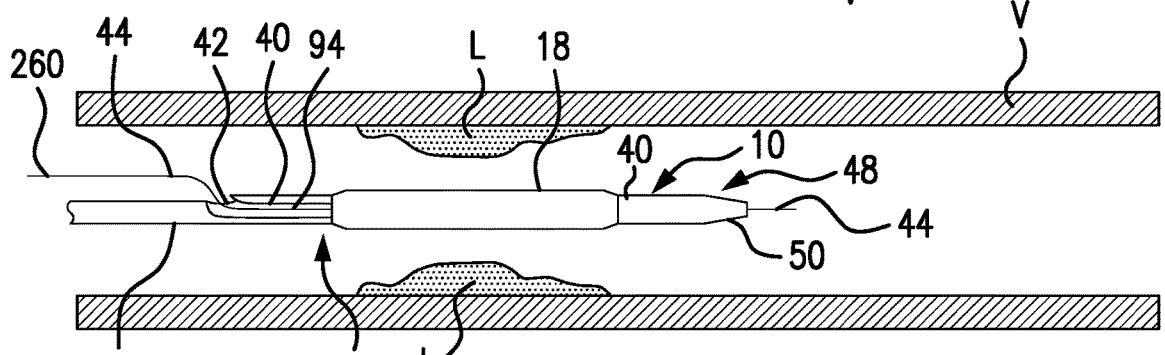

The guidewire 44, during the surgical procedure, is advanced inside the blood vessel of interest to or beyond the lesion, as shown in FIG. 11A, and subsequently, as shown in FIG. 11B, the balloon catheter 10 slides along the guidewire 44 with a guidewire inside of the inner shaft 40. The access inside the inner shaft 40 for the guidewire 44 is provided through the proximal guidewire port 42. Initially, a surgeon inserts the guidewire 44 first into the inner shaft 40 through the proximal guidewire port 42, and subsequently, advances the guidewire 44 inside the inner shaft 42 to the distal region 14 of the balloon catheter 10 and beyond a distal tip 46 of the inner shaft 40. The guidewire is advanced inside the blood vessel while holding the balloon catheter 10 outside the blood vessel, and subsequently the balloon catheter 10 slides over the guidewire (with the guidewire 42 inside the inner shaft 40) to and beyond the lesion L, as shown in FIG. 11B. The inner shaft 40 has the proximal portion 46 and the distal portion 48 with the distal tip 50 of the inner shaft 40, best shown in FIGS. 11B-11I.

The proximal portion 46 of the inner shaft 40 terminates at the proximal guidewire port 42, while the distal portion 48 of the inner shaft 40 terminating at the distal tip 50. The central portion 52 of the inner shaft 40 extends inside the balloon 18 and represents a locking portion 54, depicted in FIGS. 1A-1C, 3, 5A-5E, 6, 7A, 8A, 8B, and detailed in the following paragraphs.

As shown in FIGS. 1A-1B, 3, 7A, 7C, and 11C, a balloon inflation system 56 is coupled to the hypotube 22. The balloon inflation system 56 is fluidly connected with the internal volume or chamber of the balloon 18 through an inflation channel 58 which may extend along and within the hypotube 22 and the outer shaft 16 to controllably deliver gas or other fluid medium inside the balloon 18 with the purpose of pressurization the balloon 18 to "anchor" the guidewire 44 and the inner shaft 40 to one another, as will be detailed in further paragraphs.

The inner shaft 40 may carry marker bands for visualization of the advancement and position of the balloon during the surgical procedure.

An inflation port 64 is configured at the proximal end 24 of the hypotube 22, or at any appropriate site of the proximal region 12 of the balloon catheter 10, which is coupled through the inflation channel 58 to the interior 66 of the balloon 18.

The Luer (handle) 26 and the balloon inflation port 64 may be represented by elements used in conventional balloon catheters well-known to those skilled in the art, and are not detailed herein with further specifics. Similar to the proximal region 12 of the subject lockable balloon catheter 10, the handle 26 and the inflation port 64 may be formed from materials conventionally used in the intravascular catheters, e.g., polyethylene and/or polyterephthalate.

The lockable balloon catheter 10 preferably has a length and diameter suitable for use in a cardiac or peripheral vessel under treatment. The balloon catheter 10 may, for example, have the length ranging from 60 cm to 180 cm and a diameter ranging from 1.0 mm to 60 mm.

The balloon 18 may assume a closed (deflated) configuration (shown in FIGS. 1A and 11B, 11D, 11H, and 11I), or an inflated (expanded) configuration (shown in FIGS. 1B-1C, 2, 3, 4, 5A, 5E, 6, 7A-7C, 8A-8B, 9A-9B, and 11C, 11F-11G). Shown in FIGS. 1B-1C, the balloon 18 is depicted in an expanded (pressurized) configuration suitable for dilating the blood vessel. The balloon 18 may be formed of a noncompliant material (such as polyethylene), a semi-compliant material (such as polyterephthalate), or a compliant material (such as nylon) or some like composition.

The balloon 18 may be sized and shaped for insertion in the blood vessel as appropriate for an intended therapy and bodily lumen (blood vessel) under treatment. For example, the length of the balloon 18 may range from 1 cm to 20 cm. The balloon 18 may have a diameter, in the expanded configuration, of about 1.0 mm-6.0 mm for insertion in smaller lumens (such as coronary vessels). Alternatively, the balloon 18 may have a diameter of about 4 mm-10 mm for insertion in larger lumens (such as peripheral vessels). The balloon 18 may also have a diameter of about 1 cm-6 cm if the catheter 10 is used for the therapy associated with the thoracic or abdominal aorta.

The balloon 18 is preferably affixed to the locking portion 54 of the inner shaft 40 via thermal bonds or glue welds, as well as other suitable techniques, including the proximal balloon connection 70 and distal balloon connection 72.

The balloon 18 is configured to expand when it is controllably pressurized responsive to the introduction of a fluid (air) through the balloon inflation port 64 under control of a balloon inflation system 56. In order to pressurize the balloon 18, the balloon inflation system 56 operates to supply the fluid medium into the interior 66 of the balloon 18 from the inflation port 64 via the inflation lumen 58 (extending within the hypotube 22/outer shaft 16) to the balloon inflation port 92. For de-pressurization, the balloon inflation system 56 operates to remove the fluid medium 90 from the interior of the balloon 18 via the inflation channel 58.

Figure 2:
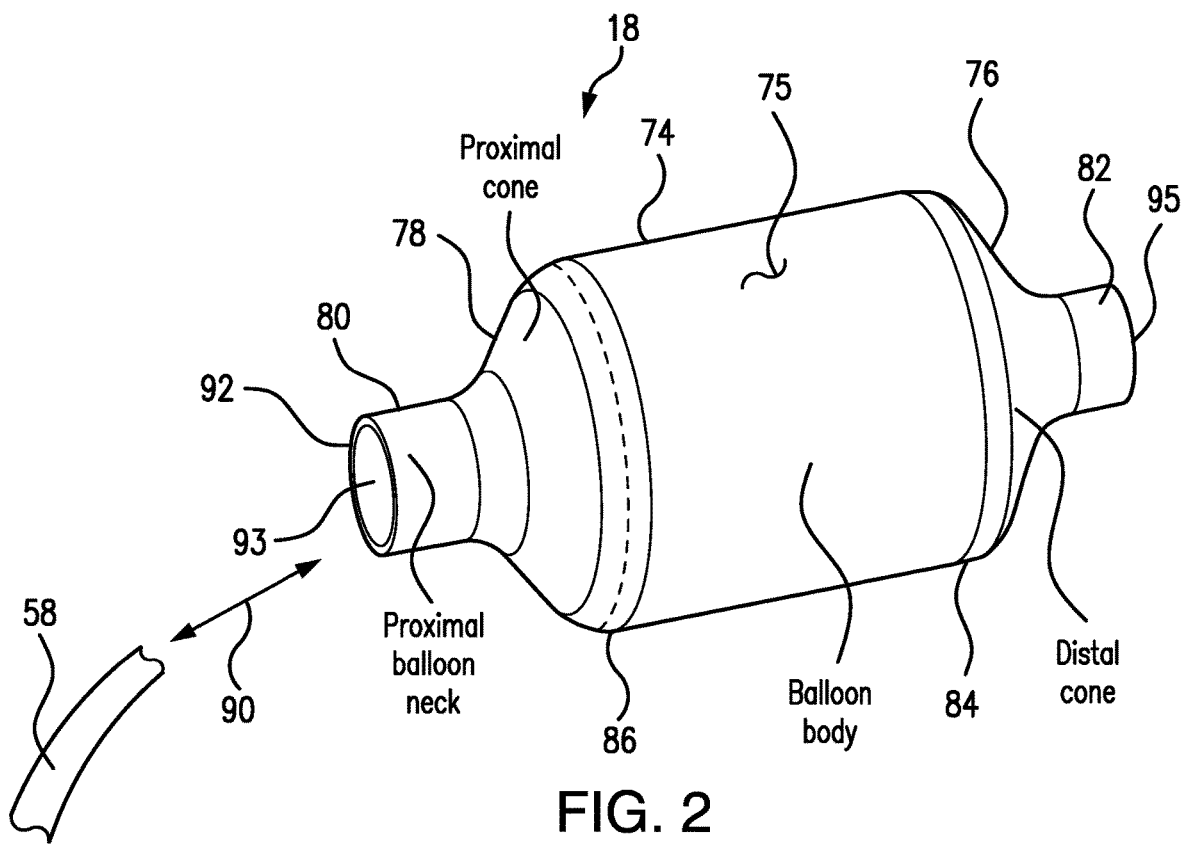
FIG. 2 is a pictorial representation of the subject balloon member.

The balloon inflation port 92 may be arranged in cooperation with the opening 93 of the proximal balloon neck 80, as depicted in FIG. 2, or at any other location on the proximal balloon neck 80, or the proximal cone 78.

As shown in FIGS. 1B-1C and 2-3, detailing the configuration of the balloon 18, such includes a balloon body 74 coupled as at distal and proximal ends to the distal cone 76 and proximal cone 78 respectively. The proximal balloon neck 80 is connected to the proximal cone 78, while the distal balloon neck 82 is connected to the distal cone 76. The proximal balloon neck 80 has a proximal balloon connection 70 (via thermal bonds, glue, weld, or other suitable techniques) with the distal portion 34 of the outer shaft 16. The distal balloon neck 82 forms a distal balloon connection 72 with the distal portion 48 of the inner shaft 40.

Figure 9A:
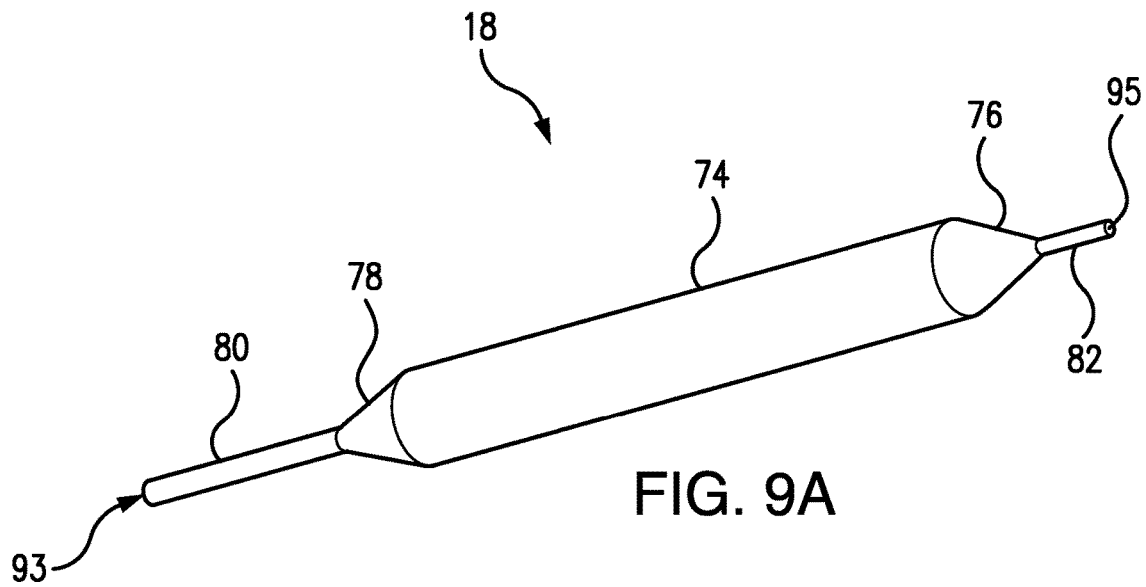
FIGS. 9A and 9B are representative of anchor balloon devoid of a smooth transition between the body and the "neck" (FIG. 9A) and with smooth transition (FIG. 9B)
Figure 9B:
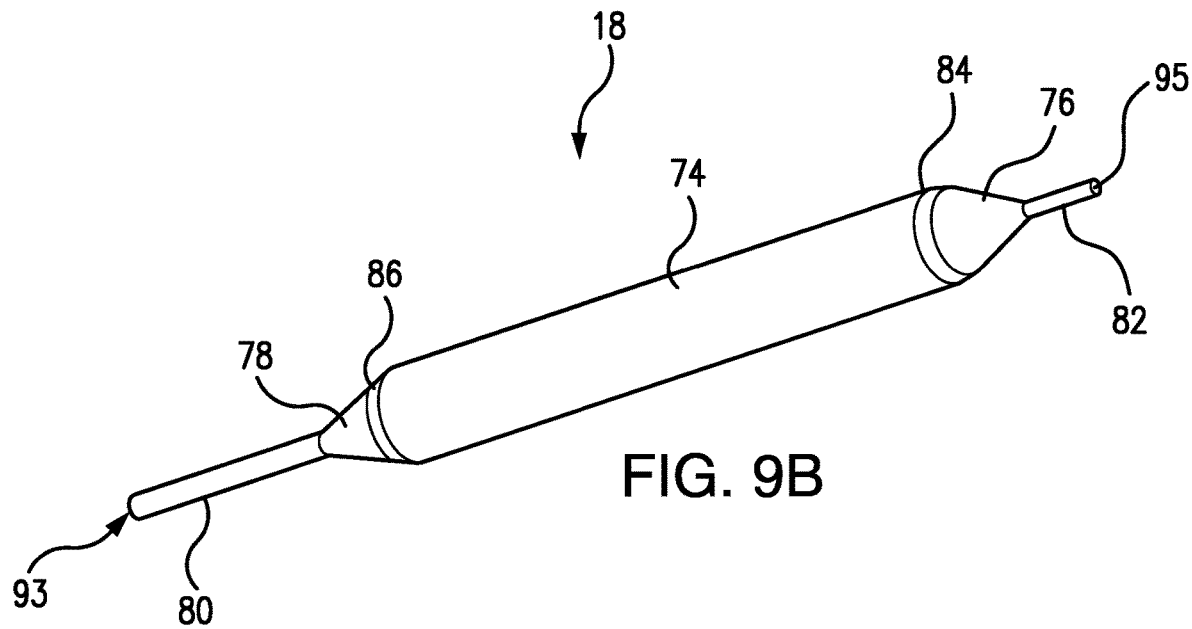

As shown in FIGS. 1B, as well as 9A-9B, the connection between the balloon body 74 with the proximal cone 78 and the distal cone 76, respectively, may be either without the smoothing of the surface as shown in FIG. 9A. However, preferably, as shown in FIG. 9B, connections between the balloon body 74 with the distal cone 76 and proximal cone 78, respectively, are through the smooth transitions 84, 86, respectively, which may, for example, have a radius of 2 mm. This creates a smooth transition between the balloon body 74 and the proximal/distal cones 78, 76 and results in a profile of the balloon beneficial for trauma-free motion of the balloon inside the blood vessel, and specifically, for removal of the catheter from the blood vessel.

In an exemplary embodiment, the length of the balloon body 74 may be about 28 mm, with a diameter of about 4 mm. The length of the proximal/distal cones may be about 4 mm (in FIG. 9A) and about 4.37 mm/4.41 mm, respectively (in FIG. 9B). The length of the proximal neck 80 may be about 10 mm, and the length of the distal neck 82 may be about 3.5 mm. The diameter of the channel 93 may be about 0.93 mm, while the diameter of the opening 95 of the distal neck 82 may be about 0.54 mm. These dimensional values are presented herein for exemplifying a specific design, and may vary in different implementations of the subject system.

The balloon inflation system 56 is operatively coupled to the inflation port 64 in a fluidly sealed fashion to support passage of the inflation fluid 90 (such as, for example, saline, iodinated contrast media, or air) to enter the balloon 18, or to exit therefrom.

The balloon inflation system 56, which is schematically depicted in FIGS. 1A-1B, 7A, 7C, and 11C, may be a manual or an automatic system. In the preferred automatic embodiment, the balloon inflation system 56 may include an electronic sub-system, a pneumatic sub-system, and a control software with a corresponding user interface. The electronic sub-system, under control of the control software, supplies power to solenoid pressure valves (which are fluidly coupled to the inflation port 64) to control the pressurizing/depressurizing cycles of the operation of the subject balloon system with the air flow.

The inflation lumen 58 is configured with and terminates, at its distal end, in a balloon inflation port 92, which is disposed within the interior 66 of the balloon 18, preferably, in proximity to the balloon's proximal neck 80 or proximal cone 78. The inflation lumen 58 extends internally of the hypotube 22 and the outer shaft 16 between the inflation port 64 and the balloon 18 to provide bi-directional passage of the fluid (air) therealong for pressurizing/depressurizing of the balloon 18, so that in the pressurized state, the balloon 18 can assume the expanded (inflated) configuration, while in the depressurized state, the balloon 18 assumes a deflated (closed) configuration.

The subject intravascular delivery system operates in conjunction with a delivery component, such as, for example, the guidewire 44. The guidewire 44 is advanced inside the blood vessel towards (and preferably beyond) the lesion site prior to the cardiac (or other intravascular) procedure. The subject intravascular delivery system is subsequently displaced along the guidewire 44 internally of the blood vessel to a position corresponding to a lesion site for pre-dilatation, or other treatment.

The lockable balloon catheter 10 is configured with a guidewire lumen 94 extending internally the inner shaft 40 between the rapid-exchange (RX) port 42 and the distal tapered tip 50 at the distal portion 48 of the inner shaft 40. The guidewire 44 extends inside the guidewire lumen 94 and extends distally beyond the distal tapered tip 50.

The guidewire lumen 94 is sized to permit the passage of the guidewire 44 therethrough. For example, the guidewire lumen 94 may be sized to permit the guidewire to be inserted therethrough to facilitate displacement of the distal region 14 of the balloon catheter 10 to a desired location along the guidewire 44 in a patient's vasculature or an organ.

The guidewire lumen 94 may be located centrally in the inner shaft 40, or alternatively, may be off-center. Preferably, the guidewire lumen 94 is compressible responsive to actuation of the balloon inflation system 56 by a clinician, e.g., inflation of balloon 18, to lock the guidewire 44 therein.

The inner shaft 40 may preferably be formed of a flexible material to facilitate compression of the guidewire lumen 94. The inner shaft 40 may be formed of a flexible material along its entire length, or along a select portion(s) of its length, such as the locking portion 54 within the balloon 18, i.e., between their proximal and distal balloon necks 80 and 82, respectively.

In the subject system, the lockable balloon catheter 10 is equipped with a locking mechanism which includes and is supported by cooperation of the balloon inflation system 56, inflation lumen 94 inside the inner shaft 40, balloon 18, and locking portion 54 of the inner shaft 40 to transform the subject system between a locked mode of operation and an unlocked mode of operation.

Figure 3:
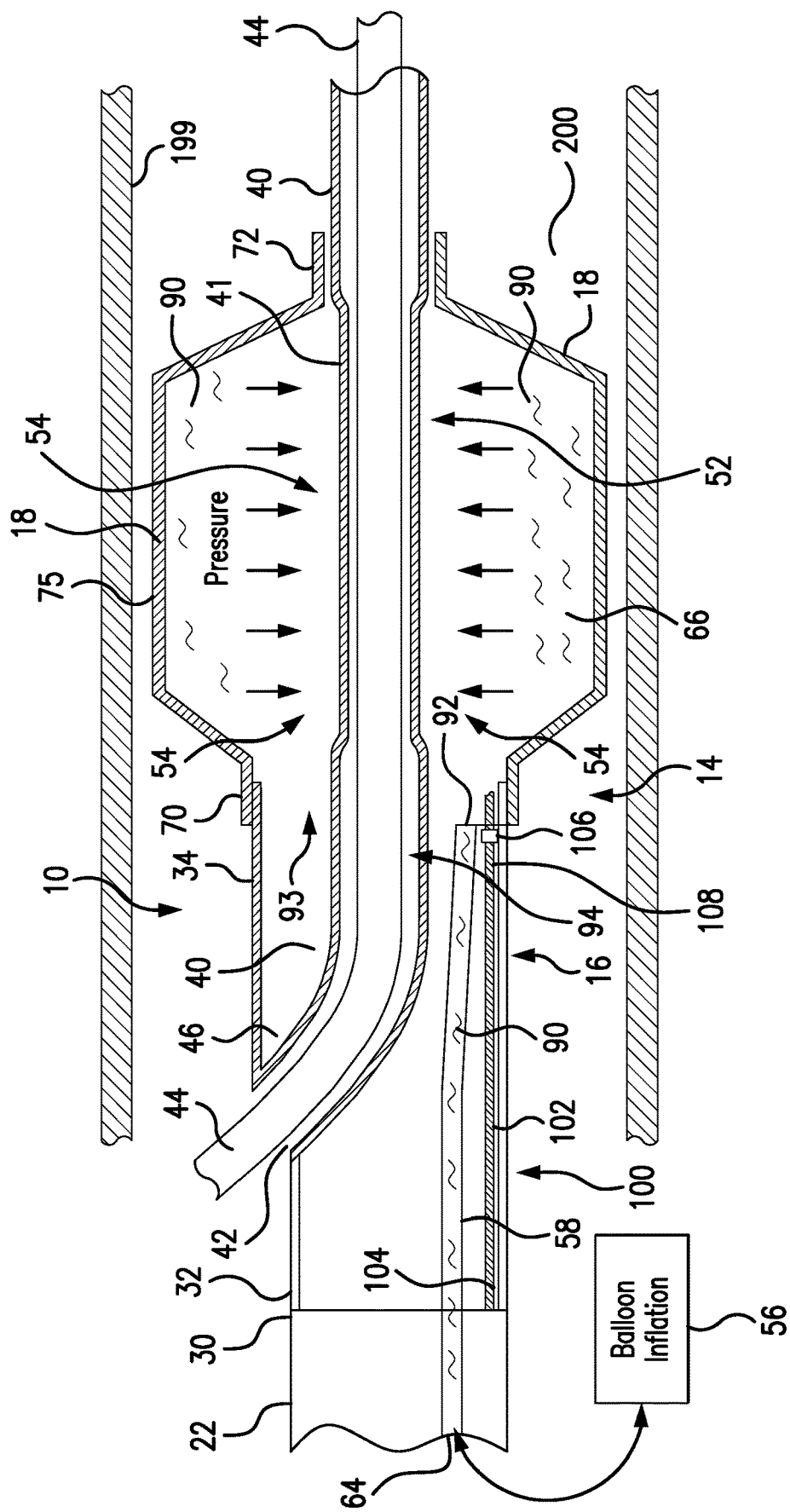
FIG. 3 is a cross-sectional elevational view of the locking mechanism.

In the locked mode of operation, the inflation of the balloon 18 is used to lock the balloon catheter 10 to the guidewire 44. As an example, the inflation of the balloon 18 at a predetermined pressure, causes the locking portion 54 of the inner shaft 40 to press against the guidewire 44 (as depicted in FIG. 3), thereby causing the walls 41 of the guidewire lumen 94 (extending inside the balloon 18) to compress around the delivery guidewire 44, thus locking the guidewire 44 within the inner shaft 40. In the compressed configuration, the contiguous coupling between the walls 41 of the guidewire lumen 94 and the guidewire 44 prevents relative displacement between the guidewire 44 and the walls 41 of the inner shaft 40. Thus, the contiguous coupling between the walls 41 of the inner shaft 40 and the guidewire 44 resulted from the controlled pressurizing of the balloon 18, as needed by the therapeutic procedure, locks (anchors) the guidewire 44 to the inner shaft 40 of the balloon catheter 10.

When the inflation system 56 of the locking mechanism deflates the balloon 18, the walls 41 of the guidewire lumen 94 (inner shaft 40) return to their original configuration, thus releasing the guidewire from the coupling with the inner shaft 40, thereby transitioning into the unlocked mode of operation. In the unlocked mode of operation, the guidewire and the inner shaft 40 are free to be displaced one relative to the other.

The RX (Rapid Exchange) port 42 is formed between the proximal portion 32 and distal portion 34 of the outer shaft 16 a short distance from the proximal end neck 80 of the balloon 18. This arrangement is beneficial for the delivery of a therapeutic delivery catheter along the guidewire 44 to a target site in a blood vessel while the balloon catheter 10 remains locked to the body lumen, as shown in FIGS. 11G-11J, and as will be detailed in further paragraphs.

For example, while a typical rapid-exchange port is conventionally displaced at least 15 cm from a balloon, the RX port 42 in the subject system may be disposed much closer, e.g., about 1-5 mm to 30 mm from the subject balloon's proximal end neck (end) 80.

The compactness of the subject structure has a beneficial result, since the guidewire 44 exits from the inner shaft 40 via the RX port 42 within the blood vessel, and the therapeutic delivery catheter can be positioned in proximity to the RX port 42 and the balloon 18 while the balloon 18 remains securely locked to the guidewire 44 in the body lumen, thus providing favorable stable conditions for stent delivery. The therapeutic delivery catheter is thus anchored and stabilized within the body lumen.

Referring to FIGS. 1B-1C, 5E, and 10A-10D, the subject balloon catheter 10 may be enhanced by a kink resistant mechanism 100. A portion of the subject system, specifically, the hypotube 22 and the inner/outer shafts 16/40 and the balloon 18, are vulnerable to possible sharp twists, buckling, and/or curving of the elongated outer shaft 16 when the inflated balloon 18 is pulled along the guidewire while another delivery device (stent) is advanced over the guidewire.

In order to prevent the unwanted deviation of the hypotube 22, as well as elongated outer shaft 16 and the inner shaft 40, from the desired straight configuration during the cardiac procedure, the subject system may be configured with the kink resistant mechanism 100. The kink resistant mechanism 100, may be formed with a Nitinol or Steel wire-like member (or stamped elongated member), also referred to herein as a core wire 102. The core wire 102 may be affixed (bonded) to the distal end 30 of the stainless steel hypotube 22 (as depicted in FIGS. 1B, and 10A-10D), and extend therefrom inside the outer shaft 16 either into the balloon 18 or to terminate in proximity to the proximal balloon neck 80.

The kink resistant mechanism 100 prevents sharp twisting, buckling, and curling of the elongated outer shaft 16 and inner shaft 40, and thus provides a robust system capable of withstanding various scenarios of cardiac procedures.

FIGS. 1B-1C, 3, as well as 10A-10D depict the detailed illustration of the Nitinol core wire 102 shown in combination with the hypotube sub-assembly.

Figure 10A:
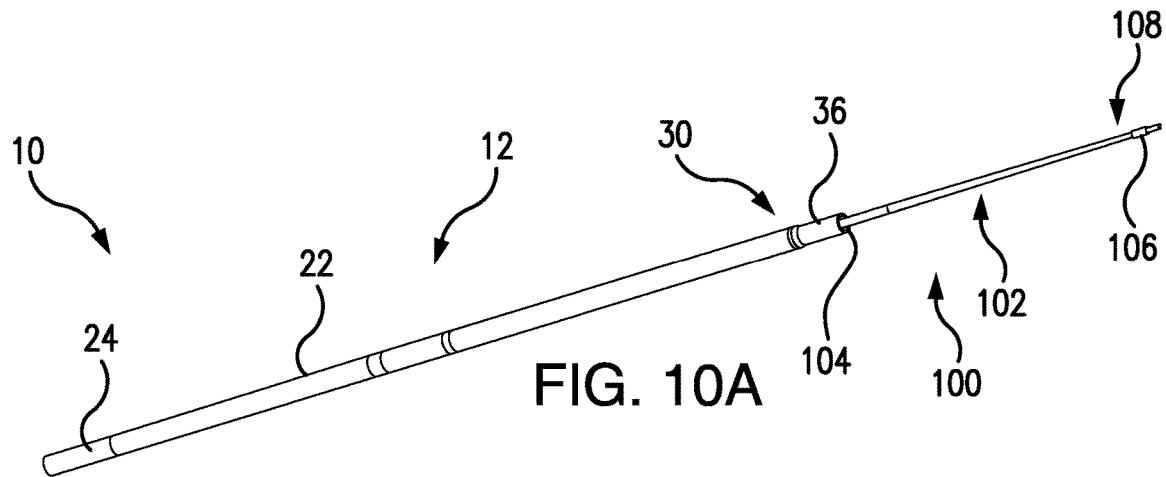
FIGS. 10A-10D are representative of the hypotube sub-assembly, with FIG. 10A showing the hypotube sub-assembly with the core equipped with a wire marker band, FIG. 10B showing the specifics of the core wire, FIG. 10C showing the specifics of the hypotube assembly in an alternative embodiment detailing the swagged segment of the hypotube, the end view of the hypotube assembly, and the swagged segment of the hypotube on an enlarged scale, and FIG. 10D showing the hypotube sub-assembly in still another embodiment with the laser cut hypotube segment welded inside of the distal end of the hypotube (full circumferential seal), and core wire welded to the distal end of the laser cut hypotube.

As specifically shown in FIG. 10A, depicting the hypotube sub-assembly 22 with the core wire 102, the distal end 30 of the hypotube 22 includes a swagged segment 36 to which the Nitinol core wire 102 is bonded by its proximal end 104. The Nitinol core wire 102 may be provided with a radiopaque marker band 106 at the distal end 108 for improved imaging of the balloon catheter location.

Figure 10B:
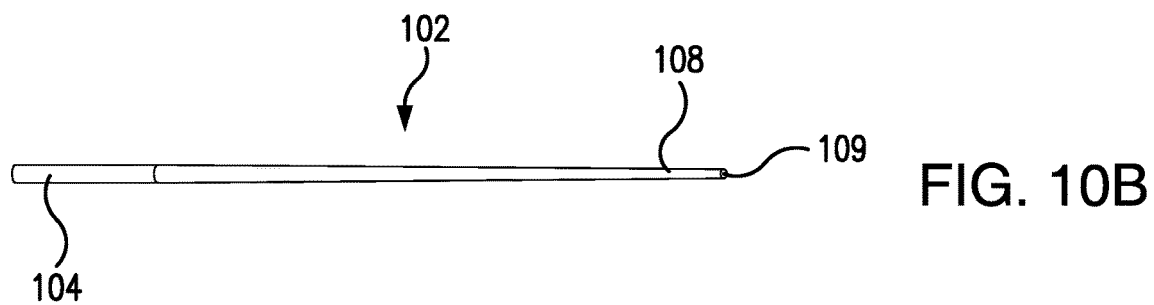

The tip 109 of the distal end 108 of the Nitinol core wire 102, as shown in FIG. 10B, is preferably blunted with a smooth arcuate surface. Such configuration on the tip 109 of the distal end 108 of the Nitinol core wire 102 is preferred to avoid sharp points which may deform or destroy the inner surface of the walls of the outer shaft, or even pierce therethrough, during the advancement of the balloon catheter in the blood vessel.

As shown in FIGS. 10A-10B, the Nitinol core wire 102 has a somewhat tapered configuration with a decreasing cross-section of the Nitinol core wire 102 in the direction from the proximal end 104, where it is coupled to the swaged segment 36 of the hypotube 22, to the distal end 106 of the core wire 102. The length of the core wire 102 may be about 38-39 cm, with the length of 10 cm at the proximal end 104 devoted for bonding to the hypotube 22. The diameter of the proximal end 104 of the core wire 102 may be approximately 0.254 inches, while the diameter of the distal end 108 of the core wire 102 may be around 0.127 inches.

Figure 10C:
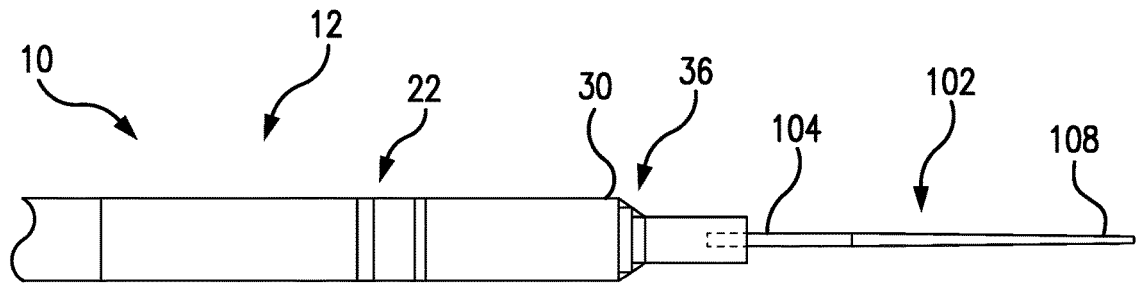

Referring to FIG. 10C, in one of the alternative embodiments, the hypotube 22 may have a length of about 108 cm with an uncoated (sand-blasted) length of about 3 cm at the proximal end 24 of the hypotube 22, followed by about 103 cm of the coated segment of the hypotube 22 extending to the beginning of the swagged segment 36 of the hypotube 22. The swagged segment 36 is preferably sand-blasted, or laser-cut, to taper the segment 36 from the outer diameter of about 0.584 mm (outer diameter of the hypotube 22) to the outer diameter of 0.508 mm (swagged segment 36). The length of the swagged segment 36 may be about 20 mm so that there is a substantial length for the proximal end 104 of the Nitinol core wire 102 to be welded to the hypotube 22 inside its swagged segment 36. The inner diameter of the swagged segment 36 may be about 0.014 inches, as shown in FIG. 10C, while the diameter of the core wire 102 may be about 0.254 inches at its proximal end 104. The dimensional values presented supra are for exemplifying a specific implementation and may vary in various alternative embodiments of the subject catheter system, dependent upon the procedure.

Figure 10D:
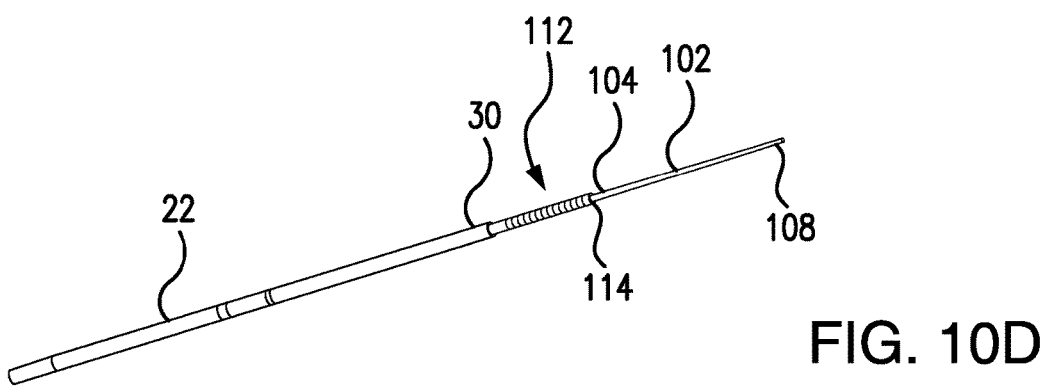

Shown in FIG. 10D, depicting an alternative implementation of the hypotube sub-assembly 22, the distal end 30 of the hypotube 22 is laser-cut. The alternative embodiment of the hypotube 22 shown in FIG. 10D has a laser-cut hypotube segment 112 which is welded inside of the distal end 30 of the hypotube 22 with the full circumferential seal therebetween. In this implementation, the proximal end 104 of the core wire 102 is welded inside the distal end 114 of the laser-cut hypotube segment 112.

The subject balloon catheter 10 may include one or more radiopaque markers to visualize positioning of the balloon catheter 10 under fluoroscopic imaging. As shown in FIGS. 1A-1C, 5E, 6, AND 10A, the subject balloon catheter 10 is equipped with at least radiopaque markers 60, 62 positioned along the inner shaft 16 in alignment with the balloon's interior 66. In addition, at least one radiopaque marker 106 is positioned on the core wire 102. The radiopaque markers may be fabricated from conventional materials, such as platinum or iridium.

The radiopaque markers 60 and 62 are positioned adjacent to the proximal end (cone) 78 and the proximal end (cone) 76 of the balloon 18, respectively, for visualization of the location of the balloon 18 in the blood vessel. The radiopaque markers 60 and 62 may be displaced about 90 and 100 cm, respectively, from the distal end (tip) 50 of the inner shaft 40. As depicted in FIGS. 1A-1C, a radiopaque marker 110 may be also positioned adjacent to the RX port 42 to permit visualization of the location of the RX port 42.

Figure 4:
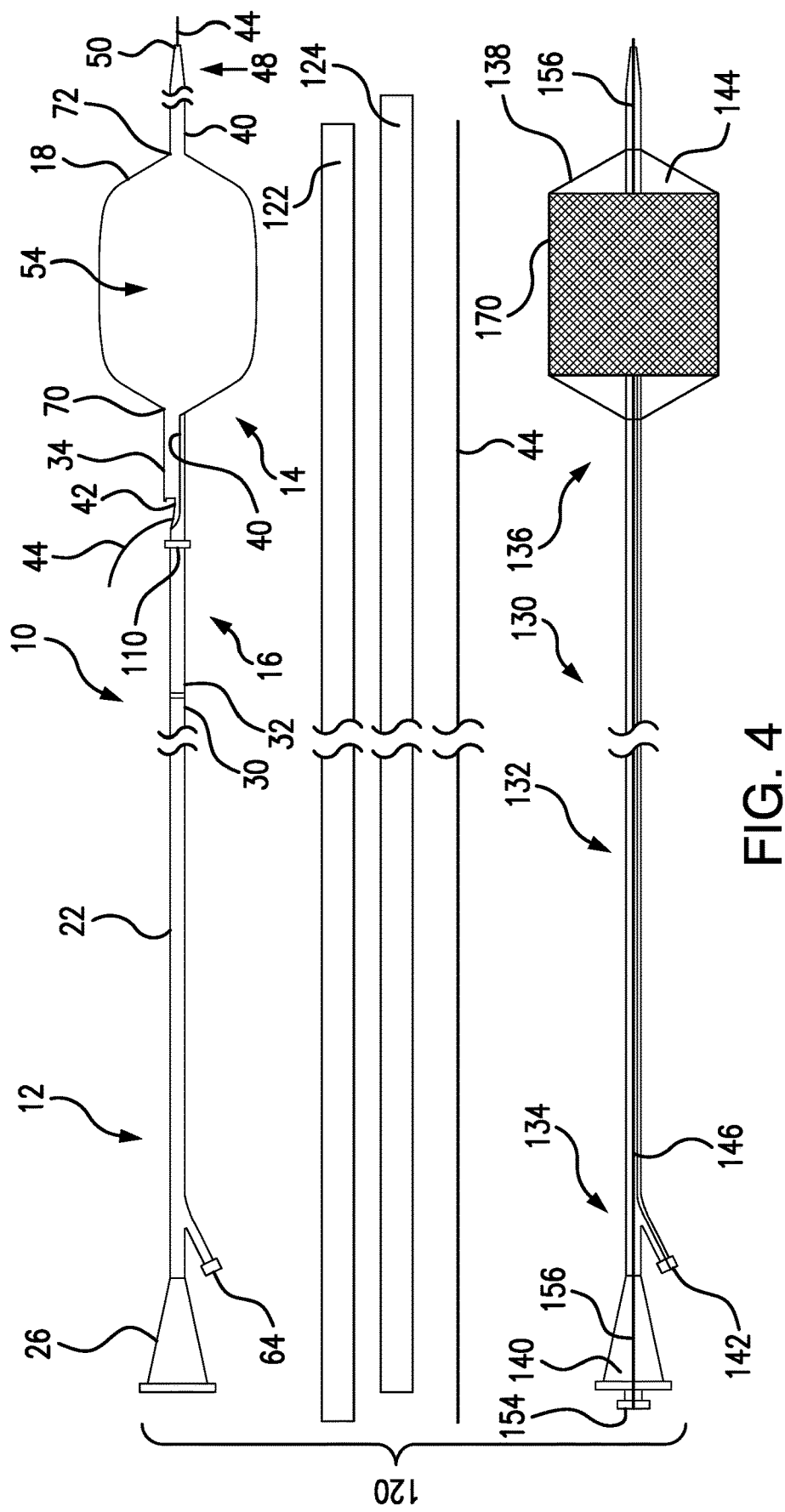
FIG. 4 is representative of an exemplary embodiment of the subject intravascular delivery system which includes a therapeutic delivery catheter, sheath, and a guidewire for use with the balloon catheter of FIGS. 1A-1C.

FIG. 4 depicts an alternative configuration of the subject intravascular delivery system 120 which uses the subject lockable balloon catheter 10. In addition to the subject balloon catheter 10, the system 120 includes a therapeutic delivery catheter, one or more sheaths, and the delivery component. In the illustrated example, shown in FIG. 4, the subject system 120 includes the lockable balloon catheter 10, a sheath 122, a sheath 124, a delivery component (guidewire) 44, and a therapeutic delivery catheter 130.

The sheath 122 is sized and shaped for intravascular delivery procedure. The sheath 122 constitutes a lumen to permit the lockable balloon catheter 10 to be disposed therein for a delivery procedure.

The sheath 124 is sized and shaped for intravascular delivery and constitutes a lumen to permit the therapeutic delivery catheter 130 to be disposed therein for the intravascular delivery. The sheaths 122 and 124 may be conventional sheaths used in intravascular procedures.

The delivery component 44 is sized and shaped for the intravascular delivery procedure, and may be a guidewire, as illustrated. In one example, the delivery component 44 is a conventional guidewire used in intravascular procedures.

The therapeutic delivery catheter 130 is designed to intravascularly deliver a therapeutic device (such as a stent) 170 to a target site in a body lumen. The therapeutic delivery catheter 130 includes an elongated shaft 132 having a proximal region 134 and a distal region 136. A balloon 138 is mounted at the distal region 136 of the elongated shaft 132.

The proximal region 134 of the elongated shaft 132 is manipulated by a clinician. For this purpose, the proximal region 134 is equipped with a handle 140. A balloon inflation port 142 is coupled to the interior 144 of the balloon 138 through an inflation lumen 146 extending internally along the elongated shaft 132.

A guidewire port 154 is coupled to the proximal region 134 of the elongated shaft 132 through a guidewire lumen 156. The guidewire lumen 156 is sized to receive the guidewire 44 therein.

The handle 140 and the ports 142 and 154 are conventional elements, and, similar to the proximal region 134 of the therapeutic delivery catheter 130, may be formed from materials conventionally used for fabrication of intravascular catheters, e.g., polyethylene or polyterephthalate. The therapeutic delivery catheter 130 preferably has a length and diameter suitable for use in the therapeutic procedures associated with cardiac or peripheral vessels.

The therapeutic delivery catheter 130 is configured to deliver a therapeutic device 170, which may be, for example, a stent. In the example, depicted in FIG. 4, the therapeutic delivery catheter 130 includes the balloon 138 disposed at a predetermined location at the distal region 136 of the elongated shaft 132 within the therapeutic device 170. When the balloon 138 is expanded (as the result of introducing the fluid, for example, air, into the balloon inflation port 142), it causes the therapeutic device 170 to expand from a delivery (deflated) configuration to a deployed (expanded) configuration.

While the therapeutic delivery catheter 130 in the intravascular delivery system 120 is depicted in the exemplary embodiment as a balloon catheter for stent delivery (e.g., bare metal stent or drug-eluting stent), the therapeutic delivery catheter 130 may also deliver other types of therapeutics and may be, for example, a drug-delivery catheter, a balloon catheter, a drug-eluting balloon catheter, or an energy delivery catheter. Exampled of various types of therapeutics may include a stent, as well as other therapeutic devices including balloon catheter(s), laser catheter(s), intravascular ultrasound (IVUS), Optical coherence tomography (OCT), drug delivery catheter(s), coil delivery catheter(s), etc. Examples of drugs that may be delivered include anti-mitotic drugs, regenerative agents, anti-inflammatory agents, anti-allergenic agents, anti-bacterial agents, anti-viral agents, anti-cholinergic agents, antihistamines, antithrombotic agents, anti-scarring agents, anti-proliferative agents, antihypertensive agents, anti-restenosis agents, healing promoting agents, vitamins, proteins, genes, growth factors, cells, stem cells, vectors, RNA, and/or DNA. The energy delivery catheter may include numerous types of energy, including the ultraviolet light, ultrasound, resistive heat, radio frequency (RF), and cryogenic.

FIG. 3 further details the longitudinal section of the subject balloon catheter 10 in its locked state. The diameter of the guidewire lumen 94 is sized to support the slidable movement (displacement) of guidewire 44 therein in the unlocked state shown in IG. 1A. The inner shaft 40 is designed to transition to the locked state (locked mode of operation) presented at least in FIGS. 1B-1C and 3, by compressing the locking portion 54 of the inner shaft 40 inside the balloon 18 to reduce the diameter of the guidewire lumen 94 when the balloon 18 is pressurized and inflated, so that the walls 41 of the inner shaft 40, at its locking portion 54, circumferentially embrace and press on the guidewire 44 to lock (anchor) the guidewire 44 within the guidewire lumen 94. For example, introduction of the fluid (air) 90 into the balloon 18 (via the inflation lumen 58 from the inflation port 64 to the balloon inflation port 92) inflates the balloon 18 and pressurizes the internal space 66 of the balloon 18 to a pressure level that compresses the walls 41 of the locking portion 54 of the inner shaft 40, as best shown in FIG. 4.

Advantageously, the inflation of the balloon 18, in addition to locking the walls 41 of the guidewire lumen 94 to the guidewire 44, may also increase the coupling of the walls 75 of the balloon 18 with the inner lining 199 of the body lumen 200, thereby anchoring the balloon 18 within the body lumen 200 to stabilize the locked guidewire 44 within the body lumen 20, as best shown in FIG. 3.

Creation of an anchoring force between the walls 41 of the locking portion 54 of the inner catheter 40 and the guidewire 44 is enhanced in the present system 41 by configuring the inner shaft 40 to further increase the gripping force between the walls 41 of the locking portion 54 of the inner shaft 40 and the guidewire 44 when inside the guidewire lumen 94 of the inner shaft 40. Specifically, some of the embodiments of the subject inner shaft 40 are depicted in FIGS. 5A-5E, as an example of numerous configurations for enhancing the anchoring effect.

As shown in FIG. 5A, the inner shaft 40A, in one modification, is configured with slots 202 spaced apart longitudinally along the walls 41A of at least the locking portion 54A of the inner shaft 40A within the balloon 18. An elastomeric layer 204 overlays the inner surface 206 on the inner shaft 40A. When the balloon 18 is pressurized via the inflation lumen 58, the pressure created by fluid (air) in the balloon 18, presses down onto the elastomeric layer 204 through the slots 202 formed in the walls 41A of the inner shaft 40A. As a result, the elastomeric layer 204 is displaced towards the guidewire 44 and locks down on the guidewire 44, thus creating an anchoring effect sought for in the present system. The pressure in the interior 66 of the balloon 18 sufficient to create an anchoring action between the walls 41A and the guidewire 44 is sufficiently lower when compared to the inner shaft having no slots/elastomeric layer 202/204.

Being able to lock down on the guidewire through the slots 202, the design shown in FIG. 5A is beneficial as it allows a lower pressurizing pressure within the balloon 18 to cause the anchoring effect.

Figure 5B:
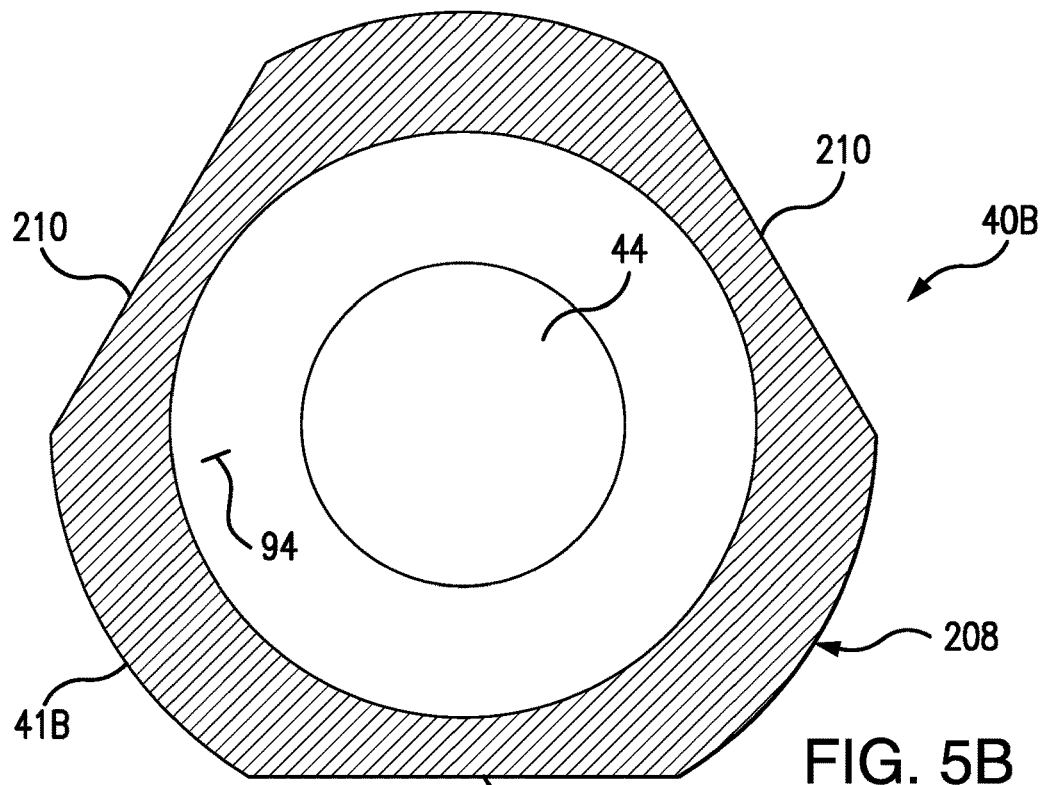

Referring further to FIG. 5B, in an alternative modification, the inner shaft 40B may be machined to reduce the thickness of the walls 41B at specific intervals about the circumference of the inner shaft 40B. Specifically, the outer surface 208 of the inner shaft 40B may be Femto lasered to create segments 210 of a reduced wall thickness. This design permits for a lower pressure in the balloon 18 to lock the guidewire 44 in position inside the guidewire lumen 94.

Figure 5C:
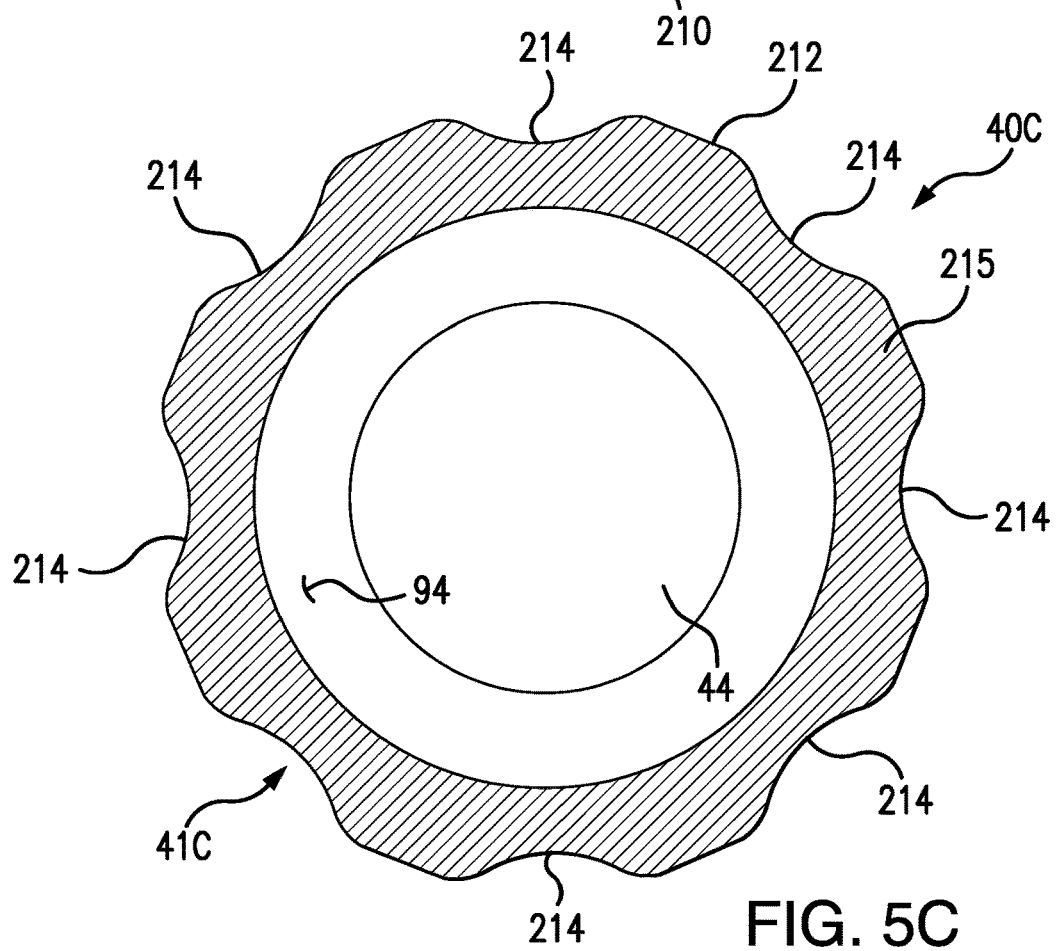

Referring to FIG. 5C, in another implementation of the present inner shaft 40C, the wall 41C is machined (for example, by laser ablation) to provide the outer surface 212 with indentations (segments) 214 which form the variable wall thickness of the inner shaft 40C. The segments 214 are spread apart along the circumference of the outer surface 212 of the inner shaft 40C. Being thinner than the thickness of the wall 41C, the segments 214 create favorable conditions for an easily collapsible inner shaft 40C. This design may be manufactured with a single lumen extrusion with sufficient cross-sectional areas 215 to maintain sufficient tensile strength while being able to be collapsible at a specific pressure within the balloon 18 to anchor the guidewire 44 inside the guidewire lumen 94 when in contact with the walls 41C of the inner shaft 40C.

Figure 5D:
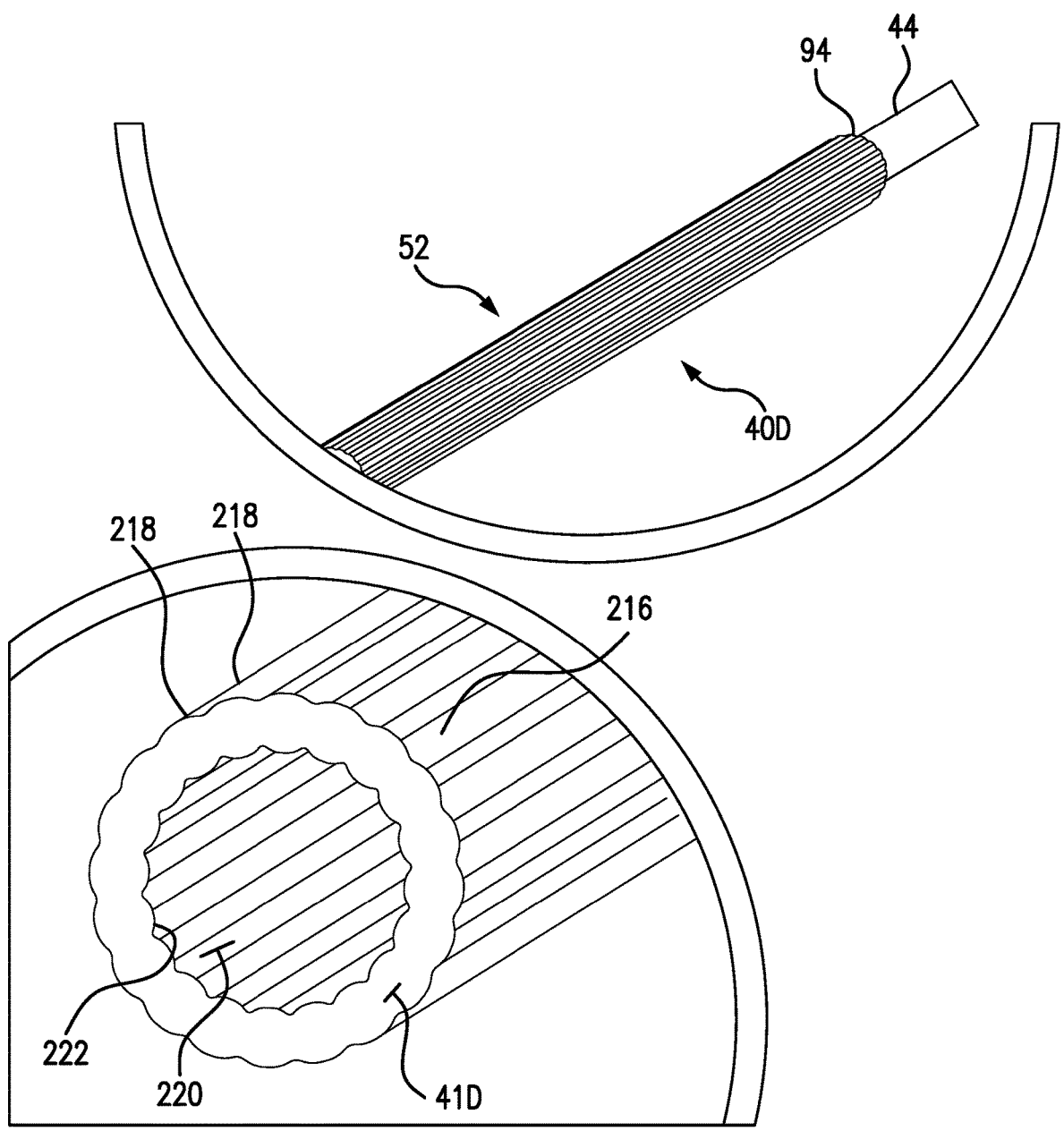

Referring further to FIG. 5D, depicting another alternative exemplary embodiment, the inner shaft 40D is machined to result in a configuration having corrugations 216 on the outer surface 218 as well as the corrugations 220 on the inner surface 222 of the inner shaft 40D. The outer surface 218 corrugated with the outer corrugations 216 is highly responsive to the pressure created in the inflated balloon, while the inner surface corrugations 220 provide an increased gripping interaction with the guidewire 44. These features in combination with the varying thickness of the walls 41D of the inner shaft 40D create a cumulative anchoring effect beneficial for lockability and controllability of the subject balloon catheter 10.

Figure 5E:
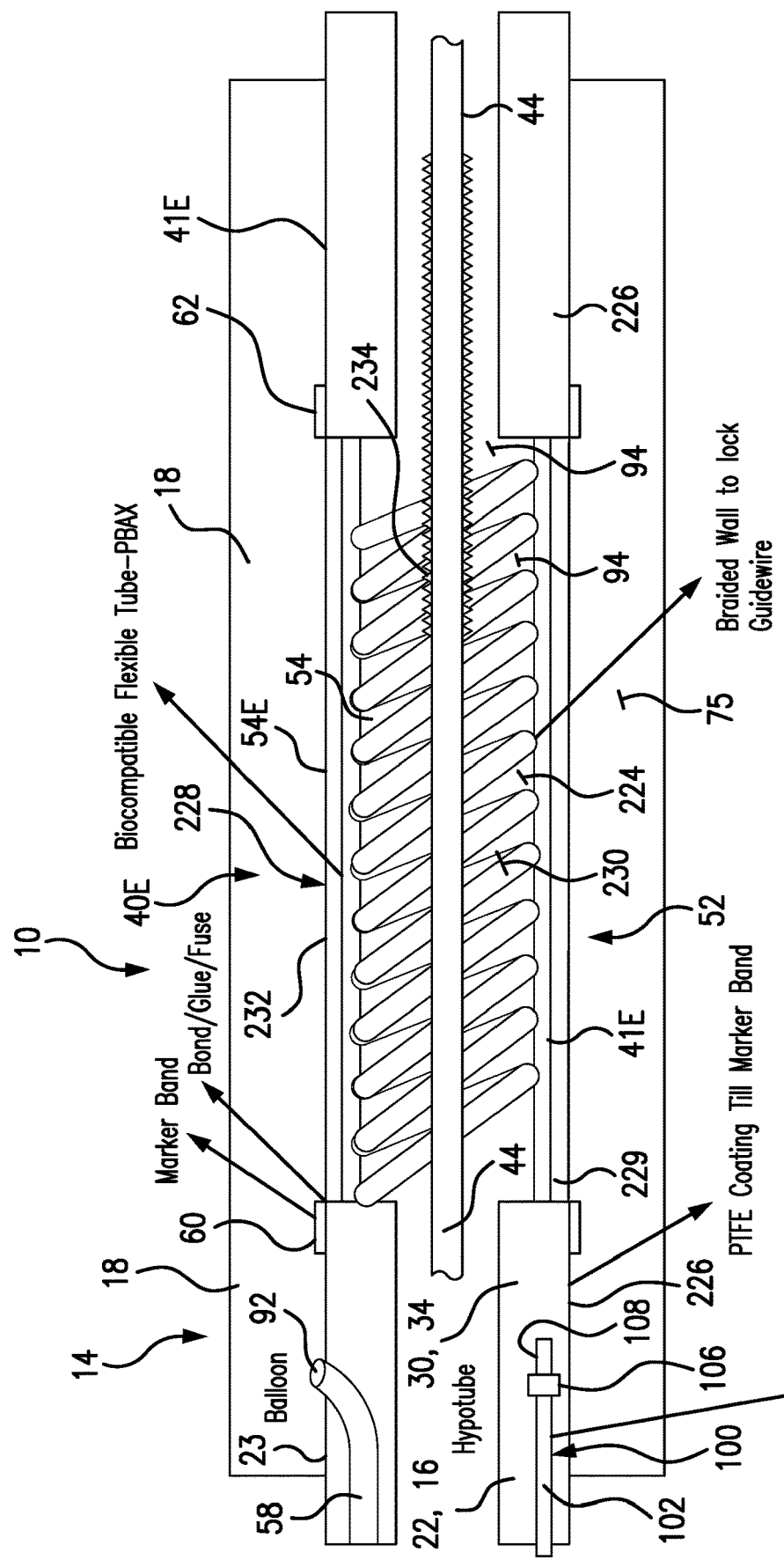

In a still further implementation for an increased gripping interaction between the lumen 94 and guidewire 44, presented in FIG. 5E, the inner shaft 40E is designed with a braided wall 224 for the enhanced lockdown to the guidewire 44. As shown in FIG. 5E, the inner shaft 40E has walls 41E and includes a locking portion or section 54E positioned in alignment with the interior 66 of the balloon 18. The locking portion 54E is formed by a flexible biocompatible tube 228 manufactured from the material such as, for example, PBAX. The inner locking portion 54E (formed by the walls 232 of the tube 228) is formed with the walls 226 bonded/glued/fused, at the distal end, to the walls 41E of the inner shaft 40E around its circumference. At the proximal end of the tube 228, its walls 232 are bonded/glued/fused to the hypotube 22 or the outer shaft 16. Marker bands 60, 62 are positioned in proximity to the distal and proximal ends of the biocompatible flexible tube 228.

In this embodiment, the hypotube 22 (or outer shaft 16) is shown coupled to the balloon 18 with the distal end 30 of the hypotube 22 bonded to the proximal end 229 of the biocompatible flexible tube 228. In an alternative embodiment, the distal end 30 of the hypotube 22 may be replaced by the distal portion 34 of the outer shaft 16.

The kink resistant Nitinol core wire 102 (with the marker band 106) extends in the distal end 30, 34 of the hypotube 22 or the outer shaft 16, respectively, towards the balloon 18 either inside the wall of the hypotube 22 or along the distal portion 34 of the outer shaft 16, as chosen for the design of the inner shaft 40E.

The inflation lumen 58, shown in FIG. 5E extends either through the wall 23 of the hypotube 22 or within the outer shaft 16, depending on the preferred implementation of this concept, and terminates in the balloon inflation port 92 which fluidly cooperates with the interior 66 of the balloon 18.

The braided wall 224 includes a braid (canted spring 230) which may interfere with the outer surface 234 of the guidewire 44 when the wall 232 of the tube 228 is radially and flexibly displaced into the guidewire lumen 94 under the pressure created in the pressurized balloon 18. The guidewire 44 may be configured with the corrugated or spring-like outer surface 234 which interferes with the braided wall 224, specifically the spring 230, overlaying the internal surface of the braided wall 224, and is locked in the anchored position between the walls 232 of the tube 228 of the inner shaft 40E and the guidewire 44, thus locking the inner shaft 40E to the guidewire 44.

Figure 6:
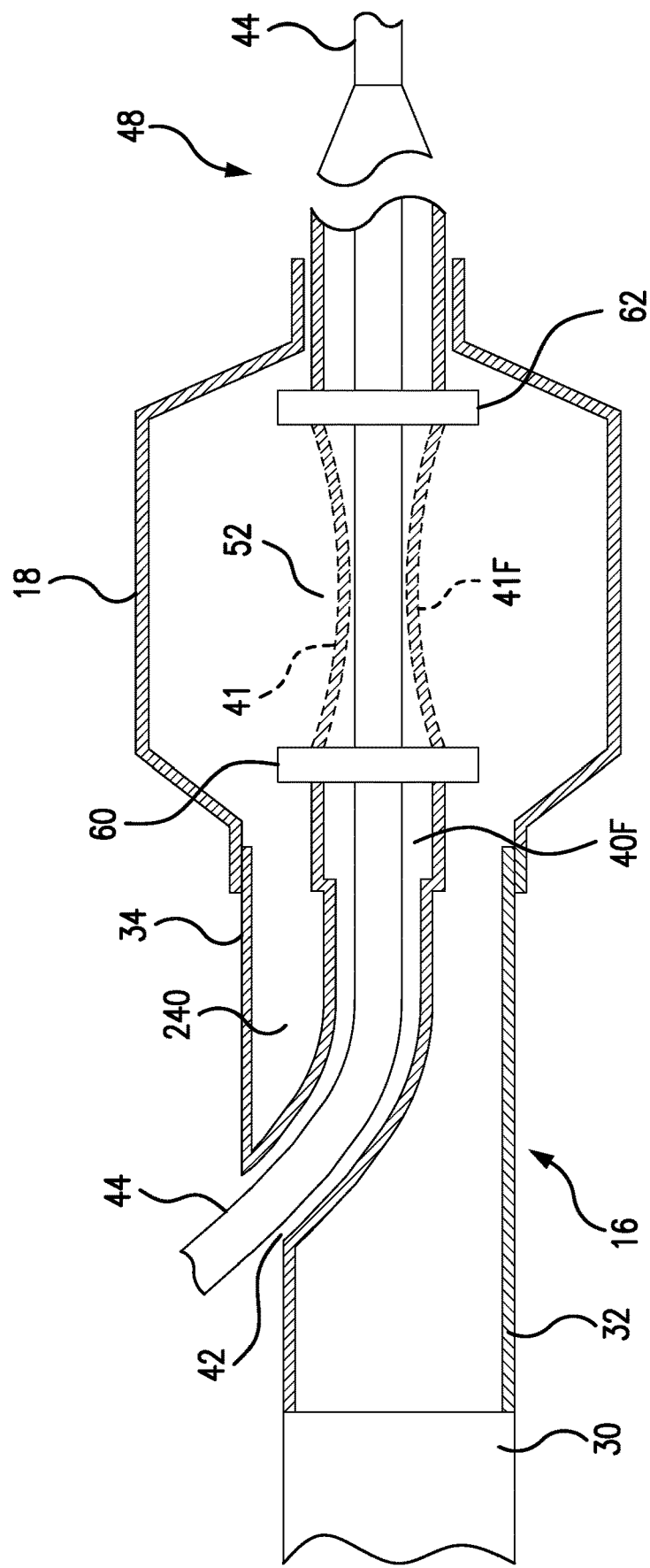
FIG. 6 depicts the inner shaft modified with a necked portion.

In another alternative implementation, shown in FIG. 6, the inner shaft 40F is depicted which may attain an increased anchoring (gripping) force between the inner shaft 40F and the guidewire 44 at the RX port 42. In this embodiment, the inner shaft 40F is configured with a necked portion 240 formed adjacent to the RX port 42. During balloon pressurization, the walls 41F of the inner shaft 40F lock down on the guidewire 44 therein, and the necked portion 240, being of a smaller diameter, further limits the motion of the guidewire 44.

Still further, for an enhanced control of the gripping force between the inner shaft 40 and the guidewire 44, the present balloon catheter 10 may use a double balloon concept presented in FIGS. 7A-7D. For example, as shown in FIGS. 7A-7B, an auxiliary smaller balloon 250 may be provided inside the main balloon 18 which may be positioned off-axis of the balloon 18 and the inner shaft 40G. The auxiliary balloon 250 has a balloon inflation port 252 for which an auxiliary inflation channel 254 is provided in coupling with the balloon inflation system 56.

The balloon inflation system 56, as shown in FIGS. 7A-7B, is equipped with two inflation channels to provide independent pressurizing of the balloons 18 and 250, as required. The inflation channel 58 provides the fluid coupling between the balloon inflation system 56 and the balloon inflation port 92 for inflating/deflating the balloon 18. The auxiliary inflation channel 254 (schematically shown in FIGS. 7A-7B) may extend between the auxiliary inflation balloon port 252 and the inflation system 56. The main balloon 18 and the auxiliary balloon 250 may be inflated either simultaneously or in sequence (independently) as required by the procedure.

In operation, while the main balloon 18 has been pressurized, in order to provide even a larger pressure onto the walls 41 of the locking portion 54 of the inner shaft 40G, the auxiliary balloon 250 may be also pressurized through the auxiliary inflation channel (lumen) 254 by inserting fluid (air) into the inflation balloon port 252. Under the additional pressure from the auxiliary balloon 250, when pressurized, the walls 41 of the locking portion 54 of the inner shaft 40G are further pressed down by the auxiliary balloon 250, thus creating an increased gripping force between the walls 41 of the locking portion 54 of the inner shaft 40G and the guidewire 44 inside the guidewire lumen 94 of the inner shaft 40G.

As shown in In FIGS. 7C-7D, the subject double balloon system in still another alternative embodiment, includes the main balloon 18 and an auxiliary balloon 260 disposed coaxially with the main balloon 18. This embodiment uses the balloon inflation port 92 to inflate/deflate the main balloon 18 and the inflation port 262 for the auxiliary balloon 260. The inflation port 92 of the balloon 18 and the inflation port 262 for the auxiliary balloon 260 are connected to the inflation system 56 through the respective channels 58 and 262, respectively. The inflation channel (or lumen) 58 for the main balloon 18 and an inflation lumen 264 for the auxiliary balloon 260 are independently actuated by the balloon inflation system 56 to inflate/deflate the balloons 18, 260, respectively. Thus, the main balloon 18 and the auxiliary balloon 260 may be pressurized by the balloon inflation system 56 in the controllable manner, either simultaneously or in sequence, as required by the procedure. The inner shaft 40H is extended within the auxiliary balloon 260, with the guidewire 44 extending inside the inner shaft 40H.

The inner shaft 40H in the implementation shown in FIGS. 7C-7D extends inside of the auxiliary balloon 260 with the locking portion 54 of the inner shaft 40H aligned with the interior 261 of the auxiliary balloon 260 and the interior 66 of the main balloon 18. When the main balloon 18 is pressurized, it may apply pressure onto the walls of the auxiliary balloon 260 which, in their turn, press down upon the locking portion 54 of the inner shaft 40H. If a larger gripping force is needed, the auxiliary balloon 260 is also pressurized, thus applying a summarized pressure from the main balloon 18 and the auxiliary 260 onto the walls of the inner shaft 40H in the controllable manner.

Figure 8A:
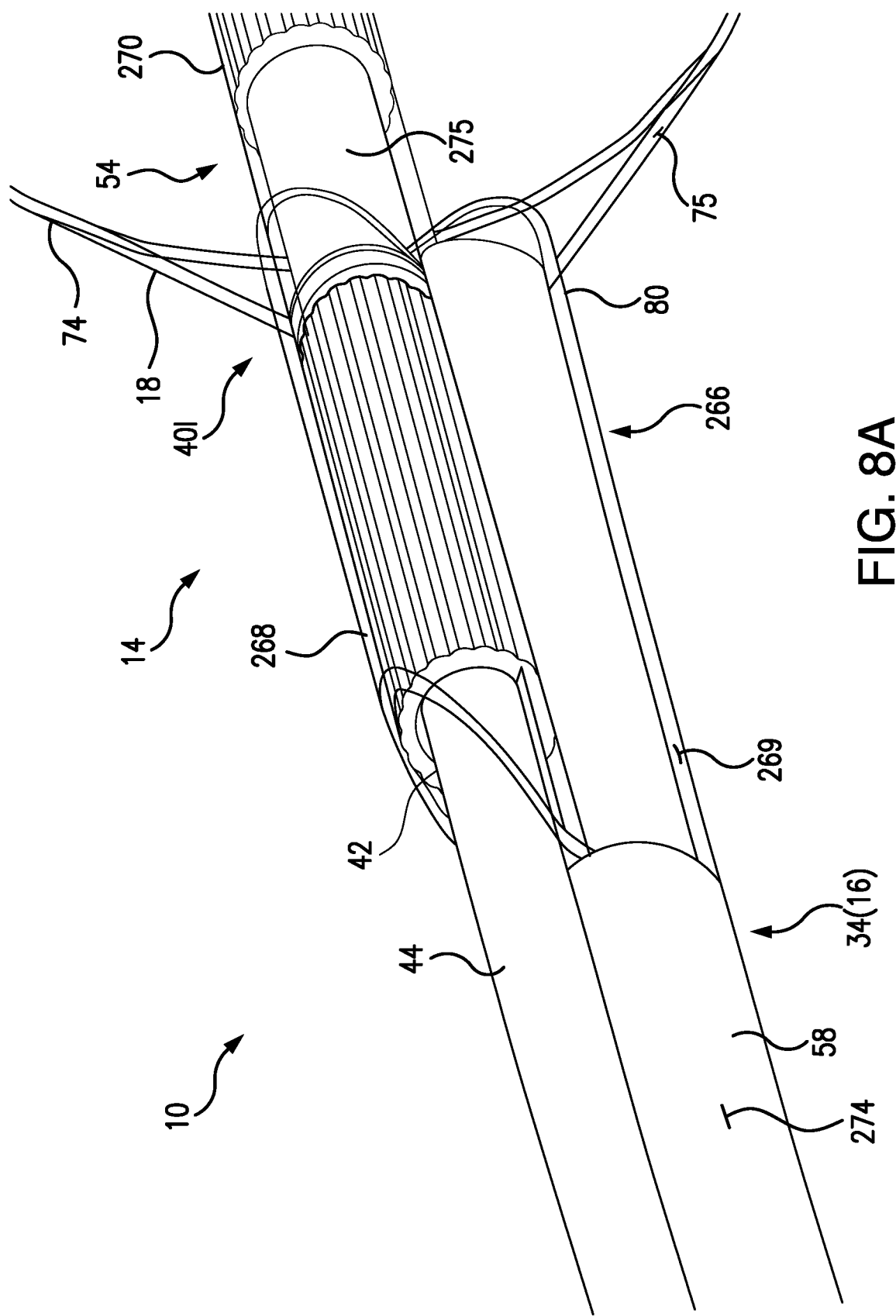

Referring further to FIGS. 8A-8B, which represent still another alternative embodiment of the present balloon catheter 10, the balloon 18 is formed with its proximal and distal ends 80, 82, respectively, in a configuration of extended "necks" fabricated from the material of the balloon 18. Although the principles of the concept and design presented in the following paragraphs are applicable both to the proximal and distal ends of the balloon 18, for simplicity of description, FIGS. 8A-8B address the proximal end 80 of the balloon 18.

The balloon 18 may be fabricated with its proximal end 82 in the configuration of the extended "neck" 266 fabricated from the balloon's material and integral with the balloon's body 74. The extended "neck" 266 forms a somewhat numeral eight-shaped configuration 267 best shown in FIGS. 8B-8C. The extended "neck" 266 includes a portion 268 embracing the inner shaft 40I as it enters the balloon 18, and a portion 269 embracing the distal portion 34 of the outer shaft 16.

The portion 269 is shaped with a concave segment 271 and a convex segment 272. The distal portion 34 of the outer shaft 16 enters the portion 269 of balloon's "neck" 266. In this implementation, the distal portion 34 of the outer shaft 16 assumes the configuration (in its cross-section) with the concave segment 273 and the convex segment 274, as depicted in FIG. 8B. The concave segments 273 and 271 of the distal end 34 of the outer shaft 16 and of the portion 269, respectively, of the balloon's "neck" 266, receive the corresponding convex portions of the inner shaft 40I and of the portion 268 in a matching aligned relationship, thus forming a reduced profile of the balloon-inner shaft/outer shaft connection at the proximal end 80 of the balloon 18.

The inner shaft 40I, in this implementation, may be configured with a long single tube (similar to the embodiments shown in FIGS. 5A-5B) or may have a number of short corrugated tubes 270 which may be spaced apart along the length of the locking portion 54 of the inner shaft 40I within and beyond the balloon 18. As an example, the inner shaft 40I is shown in FIGS. 8A-8B with corrugated tubes 270 which are spaced apart along the length of the locking portion 54 of the inner shaft 40I within the balloon 18. The guidewire 44 extends inside the guidewire lumen 94 of the inner shaft 40I.

An elastomeric sleeve 275 may be provided in the configuration of the inner shaft 40I underlying the tubes 270 to prevent pressure escape from the balloon 18. If, however, the inner shaft 40I is equipped with a single long tube instead of the numerous tubes 270, such sleeve is not needed as a single long tube can prevent the fluid leakage from the pressurized balloon.

In the configuration, shown in FIGS. 8A-8B, the proximal guidewire port 42 is shown with the guidewire 44 exiting nearly parallel to the longitudinal axis of the balloon 18. The inflation channel 58 extends in parallel to the guidewire 44 and has the cross-sectional configuration 272 (presented in previous paragraphs) which matches the profile of the guidewire 44 exiting from or entering the balloon 18.

The core wire 102 may also extend along with the inflation channel 58 formed by the distal portion 34 of the outer shaft 16. Alternatively, the core wire 102 may be embedded in the wall of the outer shaft 16.

The design principles described for the proximal end 80 of the balloon 18, are also applicable to the distal end 82 of the balloon 18, with the exception of the inflation channel which is needed only at the proximal end 80 of the balloon 18.

The configuration concept for the end(s) of the balloon 18 presented in FIGS. 8A-8C provides a reduced profile as well as a simplified fabrication process for the proximal end (as well as the distal end) of the balloon 18. The configuration presented in FIGS. 8A-8C replaces the bonding process of the balloon 18 to the outer shaft/inner shaft with the "neck" which snuggly/tightly envelopes the corresponding portions of the outer shaft/inner shaft to affix them to the balloon at one or both ends (with an optional heat shrinking). This greatly simplifies the manufacturing process. In the embodiment shown in FIGS. 8A-8C, the extended "neck" 266 formed of the balloon material and integral with the balloon body provides a steady coupling between the elements in question.

The subject method may use the subject lockable balloon catheter 10 to perform various interventional procedures. As an example, the subject method is described infra for use during an interventional procedure with the subject lockable balloon catheter 10.

In FIG. 11A, a delivery component (guidewire) is advanced inside the body lumen, for example, blood vessel, and is delivered to a target location. In this example, the delivery component 44 (illustratively, a guidewire) is placed in the vessel V at the location of a lesion L as determined by the fluoroscopic imaging technique, contrast agents and/or conventional interventional techniques.

As shown in FIG. 11B, the balloon catheter 10 is back-loaded onto the delivery component 44 by inserting the proximal end 260 of the guidewire 44 into the distal opening 262 of the guidewire lumen 84 located in the distal tip 50 of the balloon catheter 10. The catheter 10 is advanced through the patient's vasculature V until the distal region 14 is disposed at the target location (e.g., the lesion L), as determined using the radiopaque markers on the inner shaft 40 and the fluoroscopic imaging. When so disposed in a patient's vessel V, the distal region 16 of the balloon catheter 10 will appear as depicted in FIG. 11B. During the delivery procedure, the balloon 18 of the catheter 10 may be wrapped or folded in the closed configuration.

Alternatively, a delivery sheath (such as sheath 122 shown in FIG. 4) may be disposed over the distal region 14 of the balloon catheter 10 to attain a smooth outer surface for the lockable balloon catheter 10. The sheath 122 then may be retracted proximally to expose the distal region 14 once it has reached the desired location L in vessel V. As shown, the guidewire 44 is disposed in the guidewire lumen within the balloon 18 and exits the catheter 10 at the guidewire RX port 42.

Figure 11C:
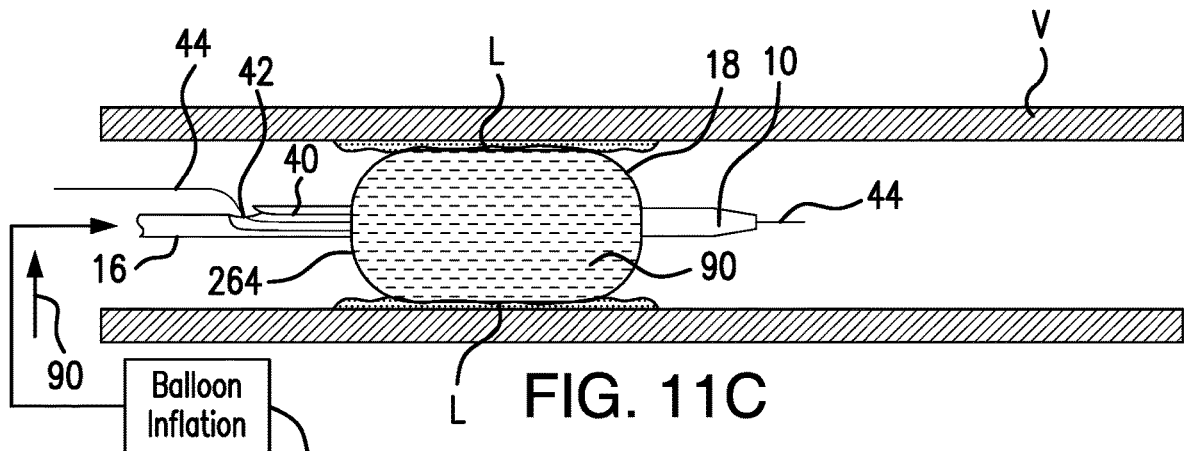
Figure 11D:
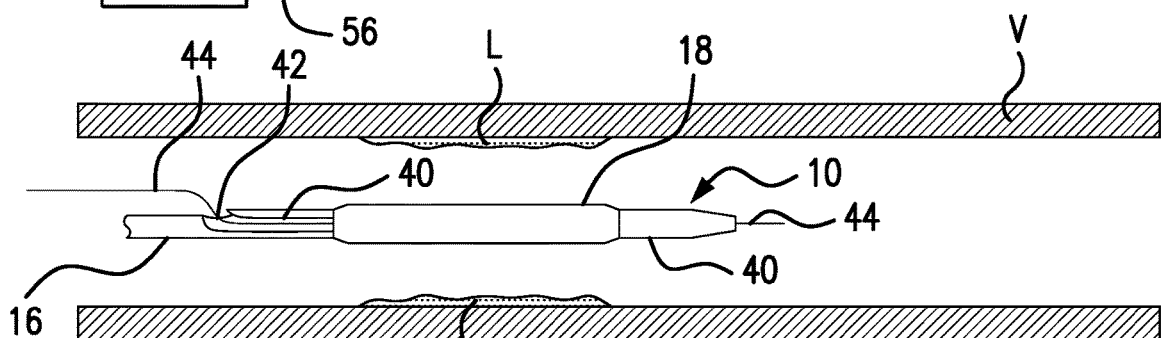

Referring now to FIGS. 11C and 1B-1C, a conventional inflator system 56 is coupled to the inflation port 64, and the inflation medium 90, such as, for example, saline or a saline diluted iodinated contrast agent, is delivered via the inflation lumen 58 to the balloon 18 to cause the balloon's expansion. In the inflated configuration, the walls 264 of the balloon 18 contact the lesion L and the intima of the vessel V to dilate the vessel V and disrupt the lesion L. Subsequently, as shown in FIG. 11D, the balloon 18 is deflated.

Figure 11E:
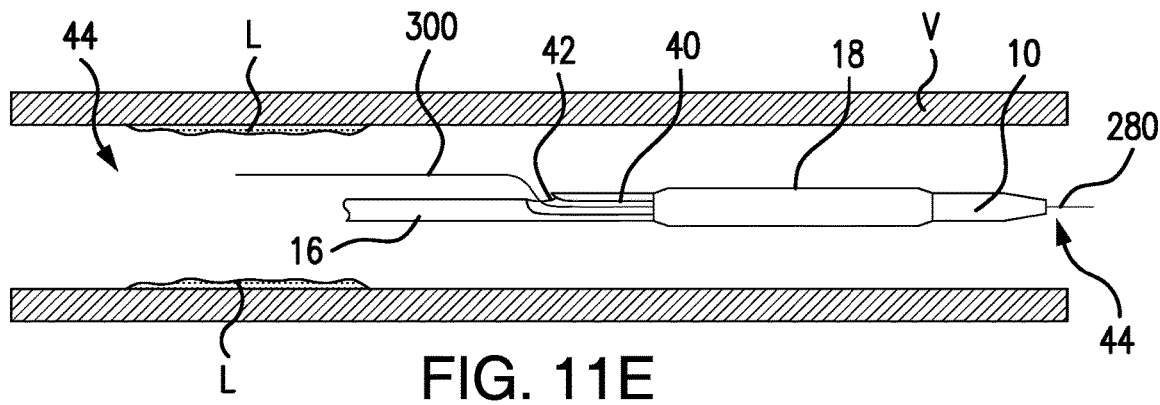

Referring now to FIG. 11E, the balloon 18, in its deflated configuration, is advanced along the distal end 280 of the guidewire 44 to a location adjacent to, but beyond, the target site L within the body lumen V. For example, the lockable balloon catheter 10 and the delivery component 44 may be moved distally within the vessel V such that the RX port 42 is disposed distal to the target site L, and the proximal end 300 of the delivery component (guidewire) 44 is located outside of the catheter 10 and extends through the target site within the body lumen V.

Figure 11F:
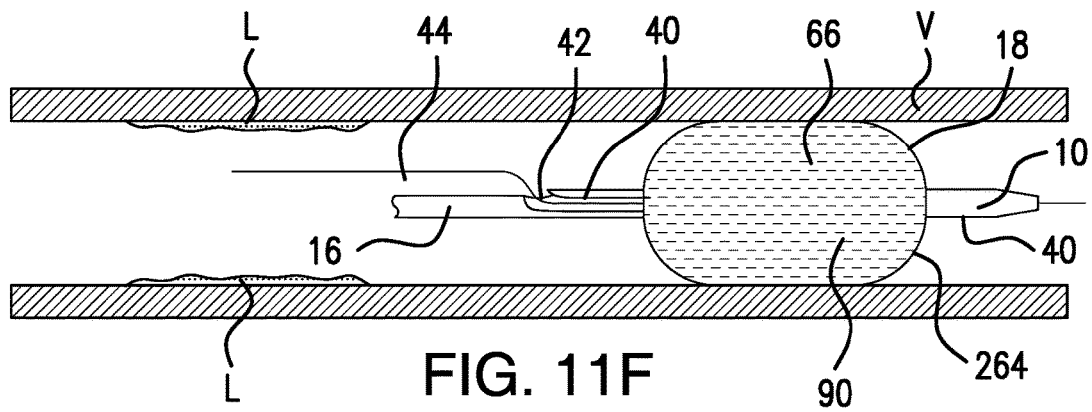

Subsequently, as shown in FIGS. 11F and 3, the balloon catheter 10 is locked to the delivery component 44 by introduction of the fluid 90 into the balloon 18 via the inflation lumen 94 and the balloon inflation port 92. Introduction of the fluid 90 under high pressure inflates the balloon 18 and pressurizes the internal space 66 of the balloon 18 to a level that compresses the inner shaft 40 and forces the guide lumen 94 into tight contact with the delivery component 44 contained therein, thus compressing around the delivery component 44 and locking the delivery component 44 to the inner shaft 40. In addition, the inflation of the balloon 18 causes the walls of the balloon in a contact with the internal lining of the vessel V, thereby anchoring the balloon 18 within the vessel V to stabilize the locked delivery component 44 within the vessel V.

Figure 11G:
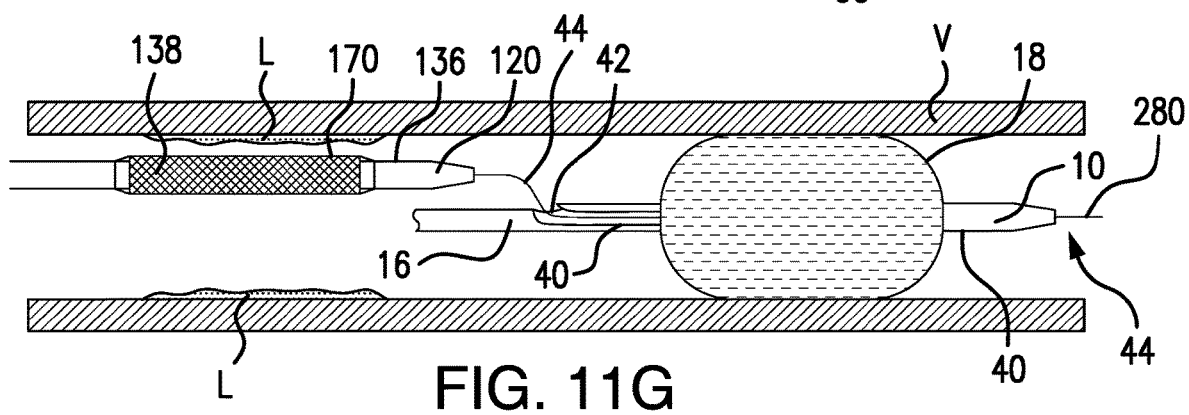
Figure 11H:
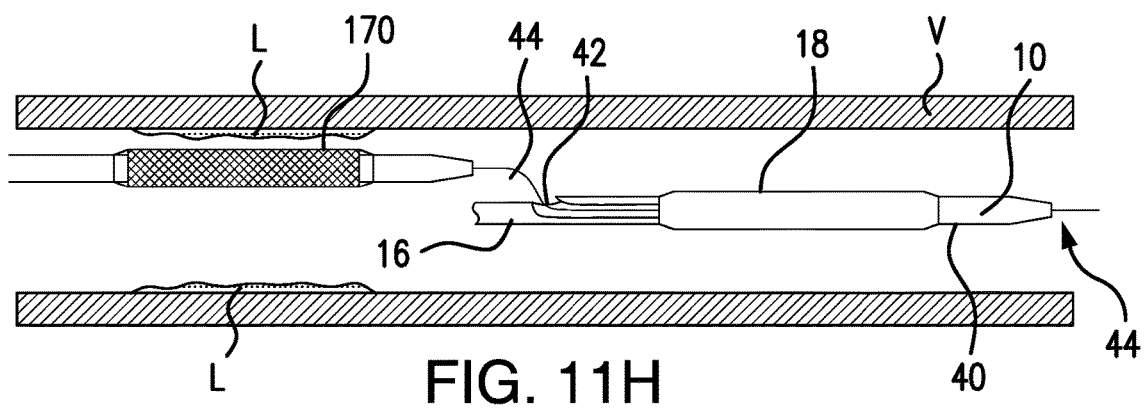

As presented in FIG. 11G, when the balloon catheter 10 is locked to the delivery component 44, and the balloon catheter 10 and the delivery component 44 are anchored in place within the body lumen (with or without contact of the walls 264 of the balloon 18 with the internal lining of the blood vessel V), the therapeutic delivery catheter 120 may be delivered along the delivery component 44 to align the therapeutic device 170 with the target site L. During delivery, the balloon 138 of therapeutic delivery catheter 120 may be folded. Alternatively, a delivery sheath (such as the sheath 124 shown in FIG. 4) may be disposed over the distal region 136 of the catheter 120 to form a smooth outer surface for the therapeutic delivery catheter 120. The sheath 124 subsequently may be retracted proximally to expose the distal region 136 once it reaches the desired location in the vessel V. In the body lumen, the lockable balloon catheter 10 remains separate from the therapeutic delivery catheter 60, although both use the same delivery component 44 in the lumen V.

Subsequently, as shown in FIGS. 11F and 3, the lockable balloon catheter 10 is unlocked from the delivery component 44. For example, deflation of the balloon 18 may result in decompression of the inner shaft 40 so that the diameter of the guidewire lumen 94, at its locking part 54, expands to permit a slidable displacement of the guidewire 44 inside the guidewire lumen.

Figure 11I:
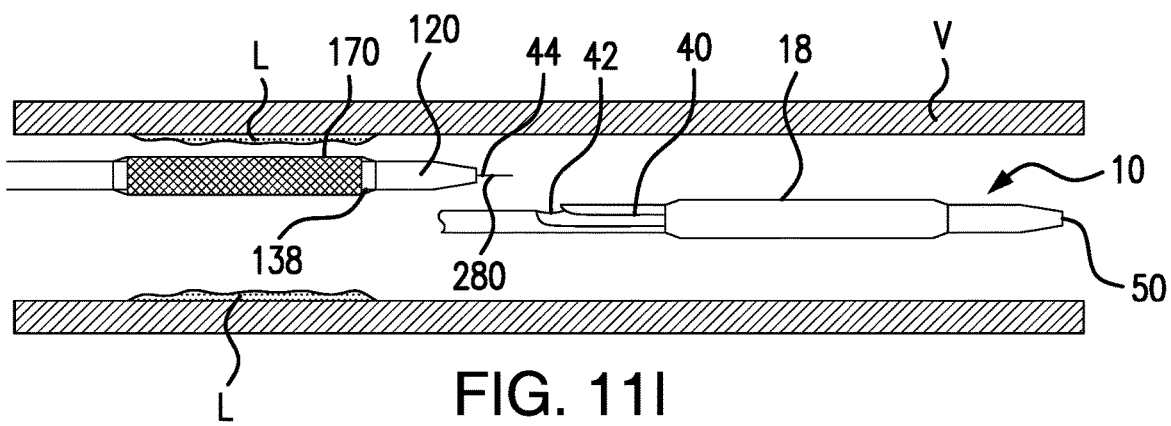

As shown in FIG. 11I, the delivery component (guidewire) 44 is then removed from the lockable balloon catheter 10. For example, the delivery component 44 may be pulled proximally while the lockable balloon catheter 10 is held in place until the distal end 280 of the delivery component 44 exits the RX port 42. Alternatively, the lockable balloon catheter 10 can be moved distally while the delivery component 44 is held in place until the distal end 280 of the delivery component 44 exits the RX port 42.

Figure 11J:
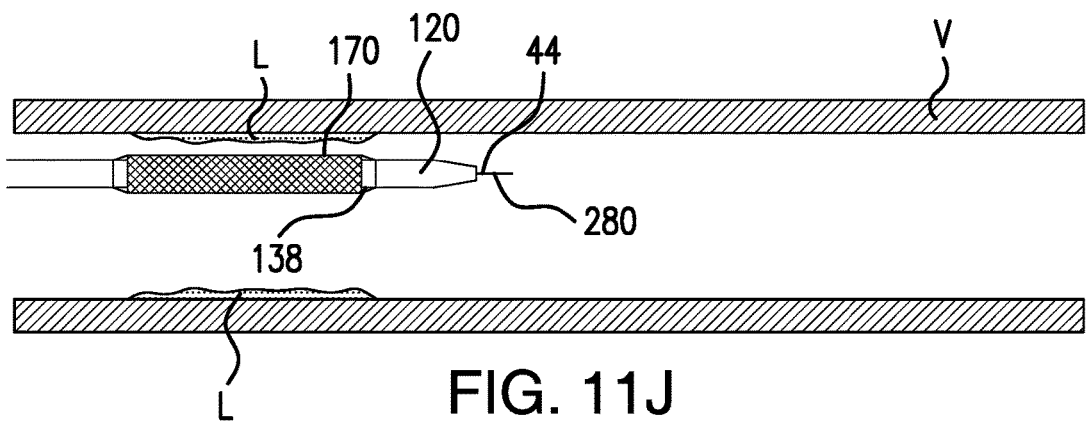

As shown in FIG. 11J, the lockable balloon catheter 10 is then displaced proximally past the target site L while the therapeutic delivery catheter 120 remains positioned at the target site L within the blood vessel V. The lockable balloon catheter 10 may be removed entirely from the patient's blood vessel V, or may be displaced a suitable proximal distance to permit the therapeutic deployment. Alternatively, the balloon catheter may be moved to a different vessel or a branch of the vessel V.

Figure 11K:
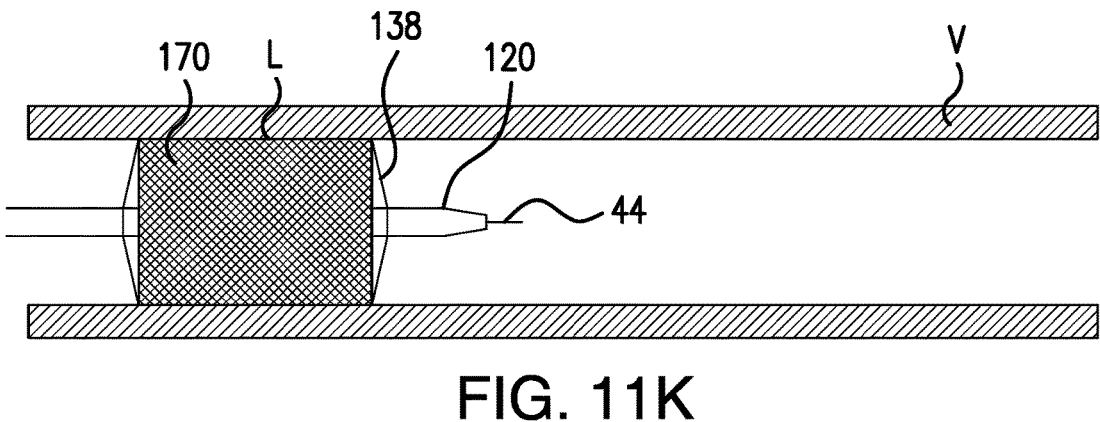

As shown in FIG. 11K, the therapeutic device, for example, a stent 170, is then deployed at the target site L. For example, the balloon 138 may be inflated to expand, thereby causing the therapeutic device 170 to expand and contact the inner wall of the vessel V. The therapeutic device 170 in the form of the stent has been depicted herein as an example, and other therapeutic devices, such as, for example, various balloon catheter(s), laser catheter(s), intravascular ultrasound (IVUS), Optical coherence tomography (OCT), drug delivery catheter(s), coil delivery catheter(s), etc., may be the examples of therapeutic devices which cooperate with the present system for therapeutic purposes as may be required by a particular surgical procedure.

Figure 11L:
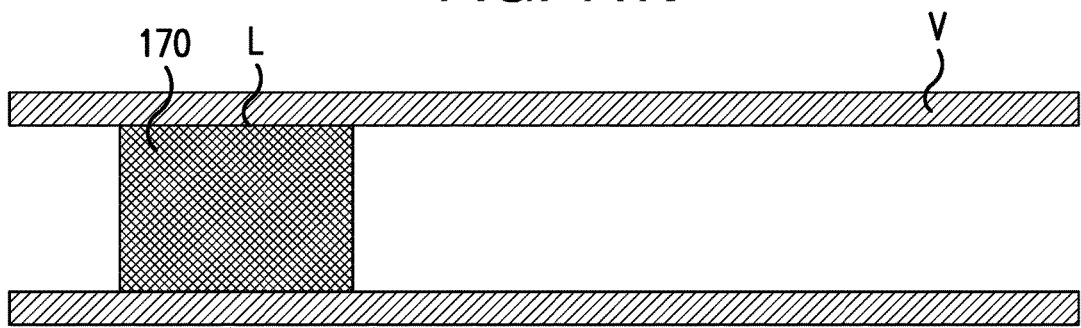

Subsequently, as shown in FIG. 11L, in the case when the therapeutic device (stent, or other therapeutic elements presented in previous paragraphs) 170 is designed for implantation, the therapeutic delivery catheter 120 is removed, leaving the therapeutic device 170 implanted at the target location L.

Although this invention has been described in connection with specific forms and embodiments thereof, it will be appreciated that various modifications other than those discussed above may be resorted to without departing from the spirit or scope of the invention as defined in the appended claims. For example, functionally equivalent elements may be substituted for those specifically shown and described, certain features may be used independently of other features, and in certain cases, particular locations of elements, steps, or processes may be reversed or interposed, all without departing from the spirit or scope of the invention as defined in the appended claims.

What is claimed is:

1. A delivery system for securely advancing a therapeutic device along a guidewire to a target site within an internal passage in a patient's body, the delivery system comprising:
a lockable balloon catheter, said lockable balloon catheter having a proximal region and a distal region, and including:
an elongated outer shaft having a proximal portion, a distal portion, and a rapid-delivery exchange port formed in walls of said elongated outer shaft between said proximal and distal portions thereof,
an inner shaft defining a guidewire lumen extending distally from said delivery port along said distal region of said at least lockable balloon catheter;
a balloon sub-system defining at least one balloon member having a balloon proximal end secured to said distal portion of said elongated outer shaft, and a balloon distal end secured to said inner shaft, and at least one inflation lumen extending within said elongated outer shaft from said proximal region of said lockable balloon catheter to said balloon sub-system, said proximal end of said balloon member being displaced from said delivery port by a predetermined distance; and
a locking mechanism operatively coupled between said balloon sub-system and said inner shaft, said locking mechanism being configured to transition walls of said inner shaft between an unlocked configuration, when a diameter of said guidewire lumen permits slidable displacement of a guidewire therein, and a locked configuration, when, responsive to inflation of said at least one balloon in said balloon sub-system, said walls of said inner shaft are compressed by a pressure inside said at least one balloon member to reduce the diameter of the guidewire lumen to form a contiguous contact with the guidewire to prevent displacement of said guidewire within the guidewire lumen.

2. The system of claim 1, wherein said balloon sub-system has at least one balloon inflation port, wherein said at least one inflation lumen is configured with and terminates in said at least one balloon inflation port positioned in proximity to said proximal end of said balloon sub-system, wherein said locking mechanism includes said balloon sub-system, said walls of said inner shaft, said at least one inflation lumen, and a balloon inflation system operatively coupled to said at least one inflation lumen at said proximal region of said lockable balloon catheter, said balloon inflation system being controlled to intermittently inflate and deflate said balloon sub-system via said at least one inflation lumen and said at least one balloon inflation port formed thereat, wherein said balloon sub-system is inflated to transition said lockable balloon catheter in said locked configuration, and wherein said balloon sub-system is deflated to transition said lockable balloon catheter in said unlocked configuration.

3. The system of claim 2, where said balloon sub-system assumes an expanded configuration in said locked configuration of said lockable balloon catheter, and wherein, in said expanded configuration, said locking mechanism is further augmented by a contact between walls of said balloon sub-system and walls of an internal passage in a patient's body between said proximal and distal ends of said balloon sub-system.

4. The system of claim 1, where said inner shaft comprises a flexible material disposed between said proximal and distal ends of said balloon sub-system to facilitate compression of at least a portion of the walls of said inner shaft extending internally of said balloon sub-system, said inner shaft being configured with at least one guidewire locking element selected from a group including:
- (a) a plurality of slots formed in a spaced apart relationship along the length of said walls of said inner shaft at least internally of said balloon sub-system and an elastomeric layer overlaying an internal surface of said inner shaft at least within said slots,
- (b) a plurality of circumferentially distributed segments of a decreased thickness formed at the walls of said inner shaft,
- (c) a flexible tube having a braided wall affixed to said inner shaft extending at least within said balloon sub-system,
- (d) at least one corrugated tube extending at least within said balloon sub-system and having corrugations formed at least at one of inner and outer surfaces of said at least one corrugated tube,
- (e) a necked portion disposed in proximity to said RX port, said necked portion having a cross-sectional dimension smaller than the diameter of said guidewire lumen; and
- (f) combinations of said elements (a)-(e).

5. The system of claim 4, wherein the flexible material comprises a braided material, wherein the braided material includes a metal, the braided material being coated with a polymer, and wherein said portion of said inner shaft between said proximal and distal ends of said balloon sub-assembly is fluidly impermeable.

6. The system of claim 1, wherein said proximal region of said lockable balloon catheter includes a hypotube and said proximal portion of said outer shaft affixed to a distal end of said hypotube, said system further comprising a kink resistant mechanism, said kink resistant mechanism being formed as a reinforcing elongated structure including at least a core wire affixed to said distal end of said hypotube and extending internally in or externally to a wall of said outer shaft in an internal or external relationship with said inflation lumen.

7. The system of claim 6, further comprising a plurality of radiopaque markers, said radiopaque marker being disposed at least at a position selected from a group including: along said inner shaft within said balloon sub-system, in proximity to said RX port, and at a predetermined position on said core wire, and a combination thereof.

8. The system of claim 6, wherein said distal end of said hypotube is configured with a swaged segment making a seamless smooth low-profile transition with said proximal portion of the outer shaft connected thereto.

9. The system of claim 6, wherein said distal end of said hypotube has a distal internal channel, said core wire being affixed to said hypotube inside of said distal internal channel.

10. The system of claim 6, wherein said core wire extends in cooperation with said at least one inflation channel or in the wall of said distal portion of said outer shaft.

11. The system of claim 1, wherein said balloon sub-system includes at least one balloon member selected from a group consisting of a first balloon member, a second balloon member, and a first and a second balloon member disposed coaxially or off-axis in relationship to one another.

12. The system of claim 1, wherein the distance between the RX port and the proximal end of the balloon ranges from 1 mm to 30 mm.

13. The system of claim 1, wherein said balloon sub-system includes an extended "neck" at least at one of said proximal end and distal end of said balloon sub-system, said extended "neck" being formed from a material of said balloon sub-system in an integral coupling with the balloon body, wherein said extended "neck" disposed at the proximal end of said balloon sub-system receives and snuggly embraces therein a portion of said inner shaft and said distal portion of said outer shaft in substantially parallel relationship to one another.

14. The system of claim 13, wherein said extended "neck" is configured with an eight-like cross-section including a first portion circumferentially embracing the portion of the inner shaft and forming said RX port thereat, and a second portion having a convex segment and a concave segment connected to one another, wherein said concave segment of said second portion of said extended "neck" receive said first portion of said extended "neck": in a closely matching relationship.

15. The system of claim 14, wherein said distal portion of said outer shaft has a cross-section formed with a concave portion and a convex portion matching said concave/convex portions of said extended "neck" of said balloon sub-system, respectively, wherein said concave portion of said distal portion of said outer shaft receives thereat the guidewire extending in said inner shaft, and wherein said at least one inflation channel extends inside said distal portion of said outer shaft.

16. The system of claim 1, wherein said delivery system is adapted for an internal passage including at least one of a blood vessel, a bile duct, and a ureteric duct.

17. An intravascular delivery system for securely advancing a therapeutic device along a delivery component to a target site within a body lumen of a patient, the system comprising:
- a lockable balloon catheter having a proximal region and a distal region, including:
- an outer shaft having a proximal portion, a distal portion, and a rapid-exchange (RX) port formed in walls of said outer portion shaft between said proximal and distal portions thereof,
- an inner shaft forming a delivery component lumen extending distally from said RX port along said distal portion of said lockable balloon catheter,
- an inflation lumen extending within the outer shaft to and along said distal region of said outer shaft;
- a balloon member having a balloon proximal end secured to said outer shaft at the distal portion thereof, and a balloon distal end secured to said inner shaft, said proximal end of said balloon being displaced from said RX port a predetermined distance;
- a locking mechanism operatively coupled between said balloon member and said inner shaft, said locking mechanism being configured to transition walls of said inner shaft between an unlocked configuration, when a diameter of the delivery component lumen permits displacement of the delivery component therein, and a locked configuration, when, responsive to inflation of said balloon member, walls of said inner shaft are compressed by pressure within the balloon member to reduce the diameter of the delivery component lumen to contact the delivery component to prevent displacement of said delivery component within the delivery component lumen; and
- a therapeutic device delivery catheter carrying a therapeutic device at a distal portion thereof and operatively coupled to said delivery component for displacement to a target site within a body lumen along said delivery component;
- whereby said therapeutic element is advanced along said delivery component to the target site within the body lumen in proximity to the RX port while said balloon is inflated and anchored within the body lumen.

18. The system of claim 17, wherein said inner shaft is formed with a flexible material within said balloon member to facilitate compression of the walls of said inner shaft, wherein said inner shaft is configured with at least one guidewire locking element selected from a group including:
(a) a plurality of slots formed in a spaced apart relationship along the length of said walls of said inner shaft at least internally of said balloon sub-system and an elastomeric layer overlaying an internal surface of said inner shaft at least within said slots,
(b) a plurality of circumferentially distributed segments of a decreased thickness formed at the walls of said inner shaft,
(c) a flexible tube having a braided wall affixed to said inner shaft extending at least within said balloon sub-system,
(d) at least one corrugated tube extending at least within said balloon sub-system and having corrugations formed at least at one of inner and outer surfaces of said at least one corrugated tube,
(e) a necked portion disposed in proximity to said RX port, said necked portion having a cross-sectional dimension smaller than the diameter of said guidewire lumen; and
(f) combinations of said elements (a)-(e).

19. A method for intravascular delivery of a therapeutic device by secure advancement along a guidewire to a target site within a blood vessel of a patient, the method comprising:
configuring at least a lockable balloon catheter having a proximal region and a distal region and including:
an outer shaft having a proximal portion, a distal portion, and a rapid-exchange (RX) port formed in walls of said outer shaft between said proximal and distal portions thereof,
a balloon sub-system having a proximal end secured to said distal portion of said outer shaft, said proximal end of said balloon sub-system being displaced from said RX port a predetermined distance,
an inflation lumen extending within said outer shaft from said proximal region of said lockable balloon catheter and said balloon sub-system,
an inner shaft configuring a guidewire lumen extending distally from said RX port and passing within said balloon sub-system; and
a locking mechanism operatively coupled between said balloon sub-system and said inner shaft, said locking mechanism being configured to transition walls of said inner shaft within said balloon sub-system between an unlocked configuration, when a diameter of the guidewire lumen permits displacement of the guidewire therein, and a locked configuration, when, responsive to inflation of said balloon sub-system, said walls of said inner shaft within said balloon sub-system are compressed to reduce the diameter of the guidewire lumen to circumferentially contact the guidewire to prevent displacement of said guidewire within the guidewire lumen;
delivering said lockable balloon catheter to the target site in the blood vessel over a guidewire;
inflating said balloon sub-system of said lockable balloon catheter to dilate the blood vessel and disrupt the lesion;
deflating said balloon sub-system, and displacing said balloon sub-system adjacent to the target site within the blood vessel;
re-inflating said balloon sub-system, thus locking said lockable balloon catheter to the guidewire;
removing said lockable balloon catheter from the blood vessel; and
delivering a second catheter over said guidewire to the target site while the lockable balloon catheter remains locked to the guidewire to anchor and stabilize the guidewire within the blood vessel within said lockable balloon catheter.

20. The method of claim 19, wherein locking of said lockable balloon catheter to said guidewire comprises the step of inflating said balloon.

* * * * *